(12) United States Patent
Ballaguet et al.

(10) Patent No.: US 9,981,848 B2
(45) Date of Patent: *May 29, 2018

(54) SULFUR RECOVERY PROCESS FOR TREATING LOW TO MEDIUM MOLE PERCENT HYDROGEN SULFIDE GAS FEEDS WITH BTEX IN A CLAUS UNIT

(71) Applicant: Saudi Arabian Oil Company, Dhahran (SA)

(72) Inventors: Jean-Pierre R. Ballaguet, Dhahran (SA); Milind M. Vaidya, Dhahran (SA); Sebastien A. Duval, Dhahran (SA); Aadesh Harale, Dhahran (SA); Anwar H. Khawajah, Dhahran (SA); Veera Venkata R. Tammana, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/418,936

(22) Filed: Jan. 30, 2017

(65) Prior Publication Data

US 2017/0137288 A1 May 18, 2017

Related U.S. Application Data

(63) Continuation of application No. 14/686,950, filed on Apr. 15, 2015, now Pat. No. 9,593,015.
(Continued)

(51) Int. Cl.
*C01B 17/04* (2006.01)
*C07C 7/11* (2006.01)
(Continued)

(52) U.S. Cl.
CPC ........ *C01B 17/0408* (2013.01); *B01D 53/047* (2013.01); *B01D 53/0462* (2013.01);
(Continued)

(58) Field of Classification Search
CPC .......... B01J 19/24; Y02C 10/08; Y02C 10/10; C01B 17/0408; C01B 17/0404;
(Continued)

(56) References Cited

U.S. PATENT DOCUMENTS 3,534,528 A 10/1970 Porter
3,896,215 A 7/1975 Bratzler et al.
(Continued)

FOREIGN PATENT DOCUMENTS

GB 2248444 A 8/1992
KR 20160143827 A * 12/2016 ............. B01J 19/24
(Continued)

OTHER PUBLICATIONS

"Sulfur Plant and Crude Distillation"; Worldwide Refinery Processing Review; Hydrocarbon Publishing Company, First Quarter 2013.
(Continued)

*Primary Examiner* — Timothy C Vanoy
(74) *Attorney, Agent, or Firm* — Bracewell LLP; Constance Gall Rhebergen

(57) ABSTRACT

An enrichment apparatus and process for enriching a hydrogen sulfide concentration in an acid gas stream to create a hydrogen sulfide rich stream for feed to a Claus. The enrichment apparatus comprises a hydrocarbon selective separation unit operable to separate the acid gas stream into a hydrocarbon rich stream and a purified acid gas stream, wherein the acid gas stream comprises hydrogen sulfide, carbon dioxide, and hydrocarbons, a hydrogen sulfide selective separation unit operable to separate the purified acid gas stream to create the hydrogen sulfide rich stream and a
(Continued)

hydrogen sulfide lean stream, the hydrogen sulfide rich stream having a concentration of hydrogen sulfide, and the Claus unit operable to recover sulfur from the carbon dioxide lean stream. The enrichment apparatus can include a carbon dioxide selective separation unit in fluid communication with the hydrogen sulfide selective separation unit, operable to separate the hydrogen sulfide rich stream.

30 Claims, 7 Drawing Sheets

Related U.S. Application Data

(60) Provisional application No. 61/980,089, filed on Apr. 16, 2014.

(51) Int. Cl.
| | | |
|---|---|---|
| C07C 7/12 | (2006.01) | |
| B01D 53/04 | (2006.01) | |
| B01D 53/047 | (2006.01) | |
| B01D 53/22 | (2006.01) | |
| B01J 19/24 | (2006.01) | |

(52) U.S. Cl.
CPC ......... *B01D 53/226* (2013.01); *B01D 53/228* (2013.01); *B01D 53/229* (2013.01); *B01J 19/24* (2013.01); *C07C 7/11* (2013.01); *C07C 7/12* (2013.01); *B01D 2257/304* (2013.01); *B01D 2257/504* (2013.01); *B01D 2257/702* (2013.01); *B01D 2257/7027* (2013.01); *B01J 2219/24* (2013.01); *Y02C 10/08* (2013.01); *Y02C 10/10* (2013.01); *Y02P 20/152* (2015.11)

(58) Field of Classification Search
CPC .. C07C 7/11; C07C 7/12; C07C 7/144; B01D 53/226; B01D 53/228; B01D 53/229; B01D 2257/304; B01D 2257/504; B01D 2257/702; B01D 2257/7027; Y02P 20/152
See application file for complete search history.

(56) References Cited

U.S. PATENT DOCUMENTS

| | | | |
|---|---|---|---|
| 4,001,386 A | 1/1977 | Klein et al. | |
| 4,507,275 A | 3/1985 | Reed | |
| 4,508,699 A | 4/1985 | Schoofs | |
| 4,589,896 A * | 5/1986 | Chen .................. | B01D 53/1462 210/640 |
| 4,659,343 A * | 4/1987 | Kelly ..................... | B01D 53/22 210/640 |
| 4,857,078 A | 8/1989 | Watler | |
| 4,978,439 A * | 12/1990 | Carnell .............. | B01D 53/0462 208/211 |
| 5,304,361 A | 4/1994 | Parisi | |
| 5,407,466 A | 4/1995 | Lokhandwala et al. | |
| 5,558,698 A * | 9/1996 | Baker .................. | B01D 53/22 423/229 |
| 5,735,936 A | 4/1998 | Minkkinen et al. | |
| 6,287,365 B1 | 9/2001 | Markovs et al. | |
| 6,387,159 B1 | 5/2002 | Butwell et al. | |
| 6,508,863 B1 | 1/2003 | Byrne | |
| 7,306,651 B2 | 12/2007 | Cieutat et al. | |
| 7,637,984 B2 | 12/2009 | Adamopoulos | |
| 7,879,135 B2 | 2/2011 | Ravikumar et al. | |
| 7,901,646 B2 | 3/2011 | Ayala et al. | |
| 7,988,767 B2 | 8/2011 | Graham et al. | |
| 8,206,669 B2 | 6/2012 | Schaffer et al. | |
| 9,593,015 B2 * | 3/2017 | Ballaguet ................ | B01J 19/24 |
| 2005/0135992 A1 | 6/2005 | Chow | |
| 2009/0092524 A1 * | 4/2009 | Ravikumar ........ | B01D 53/1462 422/171 |
| 2009/0313895 A1 | 12/2009 | Pex et al. | |
| 2010/0310439 A1 | 12/2010 | Brok et al. | |
| 2012/0085973 A1 | 4/2012 | Jiingst et al. | |
| 2012/0103185 A1 | 5/2012 | Vaidya et al. | |
| 2013/0022534 A1 | 1/2013 | Menzel | |
| 2013/0056677 A1 | 3/2013 | Bela | |
| 2013/0071308 A1 | 3/2013 | Graville | |
| 2013/0119676 A1 | 5/2013 | Milam et al. | |
| 2013/0245351 A1 * | 9/2013 | Al-Haji ..................... | C07C 7/04 585/805 |
| 2015/0299596 A1 | 12/2015 | Sethna et al. | |

FOREIGN PATENT DOCUMENTS

| | | |
|---|---|---|
| WO | 9220431 A1 | 11/1992 |
| WO | 2011124326 A1 | 10/2011 |

OTHER PUBLICATIONS

"Sulfur Plant and Refinery Aromatics Production"; Worldwide Refinery Processing Review; Hydrocarbon Publishing Company, First Quarter 2012.
B.S. Turk el al.; "Novel Technologies for Gaseous Contaminants Control"; DOE Contract No. DE-AC26-99FT40675 U.S. Department of Energy Natioanl Energy Technology Laboratory, Sep. 2001.
The International Search Report and Written Opinion for related PCT application PCT/US2015/025272 dated Jul. 7, 2015.
E. Nasato et al.; "Oxygen Enrichment of Sulfur Recovery Units to Boost Capacity, Conserve Captial, and Improve Environmental Performance"; Presented at Sour Oil and Gas Advanced Technology Conference in Abu Dhabi, Apr. 2008.
Encyclopedia of Hydrocarbons; ENI/Istituto Della Enciciopedia Italiana Fondata da Giovanni Treccani Spa 2006 vol. II Refining and Petrochemicals, Chapter 3.2, pp. 137-160.
G. Chatterjee el al.; "Poly(ether urethane) and ploy (ether urethane urea) membranes with high H2S/CH4 selectivity"; Journal of Membrane Science 135 (1997) 99-106.
I. Blume et al.; "Vapour Sorption and permeation properties of poly (dimethylsiloxane) films"; Journal of Membrane Science, 61 (1991) 85-97.
J. Norman et al.; "Oxygen: The Solution for Sulfur Recovery and BTX," Nov. 2009.
Khanmamedov; "The Family of Highsulf Process Improvement of Amine desulfurization and aftertreatment of tail gases"; Chemistry and Technology of Fuels and Oils, 2003, vol. 39, No. 6.
M. Rameshni; "Handling Difficult Feed Stocks in Sulphur Recovery Units"; Worley Parsons; pp. 1-12.
M. Rameshni; "Impurities Removal Options in Sour Gas Field Developments"; Rameshni & Associates Technology & Engineering LLC, pp. 1-21.
M. Rameshni; "Thermal Combustion Stage Criteria in SRU's Design"; Rameshni & Associates Technology & Engineering LLC.
Orme et al.; "Mixed Gas hydrogen Sulfide Permeability and Separation using supported Polyphosphazene membranes"; Science Direct Journal of Membrane Science 253 (2005) 243-249.
P. Crevier et al., "BTX: Problem and Solution- Conclusion: CBUs eliminate BTX-induced catalyst deactivation", Oil and Gas Journal, 2007, vol. 105, No. 41, pp. 82-90.
P. Crevier et al., "BTX: Problem and Solution-1: Activated Carbon Eliminates Claus deactivation problem", Oil and Gas Journal, 2007, vol. 105 No. 40, pp. 82-90.
P. Crevier, et al.; "Quantifying the Effect of Individual Aromatic Contaminants on a Claus Catalyst", The Saudi Aramco Journal of Technology; Fall Publication 2001, pp. 56-54.
P. Crevier, et al.; "Saudi Aramco Eliminates Claus Catalyst Deactivation Caused by Aromatics usingActivated Carbon"; The Saudi Aramco Journal of Technology, Summer Publication 2007, pp. 9-19.
P.D. Clark et al.; "Fundamental and Practical Aspects of the Claus Sulfur Recovery Process"; Alberta Sulphur Research Ltd., 2007.
Park et al.; "Preparation of Supported Ionic Liquid Membranes (SILMs) for the removal of acidic gases from crude natural gas"; ScienceDirect, Desalination 236 (2009) 342-348.

(56) References Cited

OTHER PUBLICATIONS

Sulfur Recovery Unit; Expansion Case Studies; Worley Parsons, Sections 6 & 7.
Sulpher, Jan.-Feb. 2009, No. 320, World Markets on p. 4.

* cited by examiner

SULFUR RECOVERY PROCESS FOR TREATING LOW TO MEDIUM MOLE PERCENT HYDROGEN SULFIDE GAS FEEDS WITH BTEX IN A CLAUS UNIT

RELATED APPLICATIONS

This application is a continuation of U.S. patent application Ser. No. 14/686,950 filed on Apr. 15, 2015, which claims priority from U.S. provisional application Ser. No. 61/980,089, filed Apr. 16, 2014. For purposes of United States patent practice, this application incorporates the contents of both the non-provisional and provisional applications by reference in their entirety.

TECHNICAL FIELD

This invention relates to a system and method for treating acid gas streams. More specifically, this invention provides a system and method for treating acid gas streams with low mole percent hydrogen sulfide. More specifically, this invention provides a system and method for treating acid gas streams with low mole percent hydrogen sulfide and BTEX contaminants.

BACKGROUND OF THE ART

A Claus unit is the primary processing system for recovering sulfur in a form of elemental sulfur from an acid gas stream containing hydrogen sulfide. Hydrogen sulfide gas occurs naturally in natural gas or is formed as a by-product in some gas processing systems. Hydrogen sulfide is highly toxic and requires removal and treatment from the gas stream. The need to efficiently process hydrogen sulfide and other sulfur containing compounds is important in reducing emissions to meet increasingly stringent fuel regulations and growing environmental concerns. Elemental sulfur is the ultimate state of recovery from sulfur containing species.

In a Claus unit, an acid gas feed stream containing hydrogen sulfide and a source of oxygen, such as air, are fed to a furnace. Acid gas feed streams have a wide range of compositions. Many acid gas feed streams originate from solvent absorption processes, such as amine absorption.

The absorption processes extract hydrogen sulfide from the by-product gases of petroleum refining, natural gas processing, and other industrial processes. Alternately, the acid gas feed stream can come from a sour water stripper unit.

Once fed to the furnace, the hydrogen sulfide undergoes partial combustion to form sulfur, sulfur dioxide, and water. To ensure efficient performance of the Claus reaction, the furnace temperature profile is maintained in the range of 850-1,200° C. To ensure full combustion of the contaminants, the temperature needs to be above 950° C. The temperature reached depends upon the other components present in the feed such as carbon dioxide ($CO_2$), water ($H_2O$), hydrocarbons, and other sulfur containing compounds. Combustible gases tend to increase temperature by means of combustion and inert gases tend to decrease temperature by means of dilution. Temperature is an important process parameter, because the conversion of hydrogen sulfide to sulfur is a function of temperature, with pressure playing a smaller role. The residence time in the furnace is typically on the order of 0.5 second.

The ratio of combustion products depends on the amount of oxygen available in the furnace. Other products formed in the furnace can include hydrogen, carbonyl sulfide, and carbon disulfide. The furnace also breaks down contaminants present in the acid gas stream, such as mercaptans.

The reaction products are fed to a first condenser, in which elemental sulfur condenses, is separated, and is collected in a sulfur pit, and the gaseous products are reheated and fed to a catalytic converter. The catalytic converter is maintained at an average temperature of about 305° C. The temperature is limited by the need to limit the exit temperature in order to avoid catalytic bed damages. In the catalytic converter, hydrogen sulfide reacts with sulfur dioxide in the presence of a catalyst and forms elemental sulfur and water. The products from the catalytic converter are fed again to a condenser in which elemental sulfur condenses and is collected in the sulfur pit. At the end of the process, an incinerator is included.

The heating, catalytic, and condensing stages can be repeated. In a conventional Claus unit, the stages are repeated a maximum of three times, with conversion of 96-98% of the hydrogen sulfide gas, depending on the feed composition. In a modified Claus unit, a tail gas treatment unit is included at the end of the process, between the final catalytic converter and the incinerator. In configurations with a tail gas treatment unit, the heating, catalytic, and condensing stages are usually only repeated twice. Modified Claus units with a tail gas treatment unit can reach up to 99.9% conversion of hydrogen sulfide into elemental sulfur. The tail gas treatment unit minimizes sulfur dioxide emissions from the incinerator.

To increase overall energy efficiency, heat capture processes can be combined with the Claus unit, such as steam generation in a waste heat boiler and the condensers.

Maintaining the temperature in the furnace is important to ensure the reaction to elemental sulfur and the destruction of other contaminants. As noted above, the furnace temperature is affected by the composition of the feed stream and significantly by the concentration of hydrogen sulfide in the feed stream. When the concentration of hydrogen sulfide in the acid gas stream is below about 55% by volume, the temperature profile in the furnace is reduced. The concentration of the hydrogen sulfide is affected by the amount of contaminants present in the acid gas. The type and amount of contaminants are affected by the source that generated the acid gas, and by the processing steps that produced the acid gas for processing in the Claus unit.

Contaminants in the feed stream include hydrocarbons. Hydrocarbons pose several problems for a Claus unit. First, it is not clear that hydrocarbons will fully combust because the C—H bond is generally stronger than the S—H bond, thus some hydrocarbons get carried through the furnace to the catalytic units. Second, the hydrocarbons have the potential to contribute to competing side reactions to produce carbon monoxide (CO), carbon disulfide ($CS_2$), carbonyl sulfide (COS), and elemental carbon. Third, for some hydrocarbon combustion processes, such as those involving benzene, toluene, ethyl benzene, or xylene (BTEX or BTX), the furnace must be maintained at a high temperature. If the furnace temperature is too low due to a low concentration of hydrogen sulfide, the temperature may not be sufficient for BTEX degradation reactions to occur. BTX removal is important because BTX has a plugging effect on the catalyst in the catalytic converters. Catalyst poisoning from carbon compounds in the catalytic beds results in a loss of activity and high pressure drop requiring frequent catalyst rejuvenation and replacement.

Currently, several processes exist for addressing these concerns, but they all suffer from drawbacks. Acid gas bypass or split flow is used when the concentration of hydrogen sulfide is low in the feed stream. In a split flow operation, part of the stream is sent to the furnace of the Claus unit while the remaining portion of the stream is sent directly to the catalytic converters. Split flow suffers two drawbacks. First, there is an upper limit of two-thirds of the feed gas for bypass, requiring the furnace to operate under reducing conditions. Second, the increased presence of contaminants decreases the efficiency of the catalytic converters and contributes to catalytic deactivation and plugging.

Activated carbon can be used to separate BTEX from a process stream, but requires regeneration of the activated carbon, resulting in changing feed conditions to the Claus unit during the regeneration process, or shut down of the feed all together. Amine or solvent enrichment processes use solvent absorption to enrich the hydrogen sulfide concentration. Amine enrichment suffers because it introduces liquids to the process, requires significant maintenance, and requires a significant amount of energy for the operation and for the solvent regeneration.

Oxygen or air enrichment may enhance the flame temperature in the Claus unit, but requires expenditures for additional oxygen and oxygen recovery units. Natural Gas injection to the furnace can also enhance the temperature, but may increase the amount of contaminants entering the feed and components for potential competing side reactions and can increase the size of Claus unit. Methods of preheating the feed gas to ensure the temperature in the furnace require additional energy consumption adding substantially to the cost.

Therefore, a process which enriches the concentration of hydrogen sulfide in the acid gas stream and removes contaminants without requiring excessive amounts of energy, equipment and materials, or process shutdown is desired. Preferably, such a process, would maintain the overall sulfur capacity of the Claus unit, while increasing the overall sulfur recovery efficiency due to eliminated or reduced contaminants.

SUMMARY

This invention relates to a system and method for treating acid gas streams. More specifically, this invention provides a system and method for treating acid gas streams with low mole percent hydrogen sulfide. More specifically, this invention provides a system and method for treating acid gas streams with low mole percent hydrogen sulfide and BTEX contaminants.

In one aspect of the present invention, an enrichment apparatus for enriching a hydrogen sulfide concentration in an acid gas stream to create a hydrogen sulfide rich stream for feed to a Claus unit is provided. The enrichment apparatus includes a hydrocarbon selective separation unit, the hydrocarbon selective separation unit operable to separate the acid gas stream into a hydrocarbon rich stream and a purified acid gas stream, wherein the acid gas stream includes hydrogen sulfide, carbon dioxide, and hydrocarbons. The enrichment apparatus also includes a hydrogen sulfide selective separation unit in fluid communication with the hydrocarbon selective separation unit, the hydrogen sulfide selective separation unit operable to separate the purified acid gas stream to create the hydrogen sulfide rich stream and a hydrogen sulfide lean stream, the hydrogen sulfide rich stream having a concentration of hydrogen sulfide. The enrichment apparatus further includes the Claus unit in fluid communication with the hydrogen sulfide selective separation unit, the Claus unit operable to recover elemental sulfur from the hydrogen sulfide rich stream.

In certain aspects of the present invention, the enrichment apparatus further includes a carbon dioxide selective separation unit in fluid communication with the hydrogen sulfide selective separation unit, the carbon dioxide selective separation unit operable to separate the hydrogen sulfide rich stream to create a carbon dioxide rich permeate and a hydrogen sulfide rich retentate, the hydrogen sulfide rich retentate having a concentration of hydrogen sulfide. In certain aspects of the present invention, the hydrogen sulfide selective separation unit is selected from the group consisting of polyphosphazene type polymer membranes, polyether-polyamide copolymer membranes, ionic liquid membranes, ionic liquid membrane contactors, and combinations thereof. In certain aspects of the present invention, the carbon dioxide selective separation unit is selected from the group consisting of an amorphous fluoroplastic membrane, an amorphous perfluoropolymer membrane, a random fluorocopolymer membrane, a perfluorinated copolymer membrane, and combinations thereof. In certain aspects of the present invention, the hydrocarbon selective separation unit comprises a polydimethylsiloxane (PDMS) type rubbery polymer membrane. In certain aspects of the present invention, the acid gas stream further comprises contaminants selected from the group consisting of mercaptans, thiols, carbonyl sulfide, carbon disulfide, and combinations thereof. In certain aspects of the invention, non-sulfur containing contaminants can also be present. In certain aspects of the present invention, the hydrocarbon rich stream comprises benzene, toluene, ethyl benzene, and xylene. In certain aspects of the present invention, the hydrogen sulfide concentration in the acid gas stream is between 15% to 55% by volume. In certain aspects of the present invention, the concentration of hydrogen sulfide in the hydrogen sulfide rich stream is greater than 55% by volume.

In a second aspect of the present invention, a process for enriching a hydrogen sulfide concentration in an acid gas stream to create a hydrogen sulfide rich stream for feeding to a Claus unit is provided. The process including the steps of feeding the acid gas stream to a hydrocarbon selective separation unit, the acid gas stream includes hydrogen sulfide, carbon dioxide, and hydrocarbons, separating the acid gas stream in the hydrocarbon selective separation unit to create a hydrocarbon rich stream and a purified acid gas stream, feeding the purified acid gas stream to a hydrogen sulfide selective separation unit fluidly connected to the hydrocarbon selective separation unit, the hydrogen sulfide selective separation unit operable to separate the purified acid gas stream, and separating the purified acid gas stream in the hydrogen sulfide selective separation unit to create the hydrogen sulfide rich stream and a hydrogen sulfide lean stream, the hydrogen sulfide rich stream having a concentration of hydrogen sulfide, and feeding the hydrogen sulfide rich stream to a furnace of the Claus unit, the Claus unit operable to separate elemental sulfur from the hydrogen sulfide rich stream to create an elemental sulfur stream and a waste gas stream.

In certain aspects of the present invention, the process further includes the steps of feeding the hydrogen sulfide rich stream to a carbon dioxide selective separation unit in fluid communication with the hydrogen sulfide selective separation unit, the carbon dioxide selective separation unit operable to separate the hydrogen sulfide rich stream, separating the hydrogen sulfide rich stream to create a carbon dioxide rich permeate and a hydrogen sulfide rich retentate, the hydrogen sulfide rich retentate having a concentration of hydrogen sulfide, and feeding the hydrogen sulfide rich retentate to the furnace of the Claus unit. In certain aspects of the present invention, the hydrogen sulfide selective separation unit is selected from the group consisting of polyphosphazene type polymer membranes, polyether-polyamide copolymer membranes, ionic liquid membranes, ionic liquid membrane contactors, and combinations thereof. In certain aspects of the present invention, the carbon dioxide selective separation unit is selected from the group consisting of an amorphous fluoroplastic membrane, an amorphous perfluoropolymer membrane, a random fluorocopolymer membrane, a perfluorinated copolymer membrane, and combinations thereof. In certain aspects of the present invention, the hydrocarbon selective separation unit comprises a rubbery membrane. In certain aspects of the present invention, the acid gas stream further comprises contaminants selected from the group consisting of mercaptans, thiols, carbonyl sulfide, carbon disulfide, and combinations thereof. In certain aspects of the present invention, the hydrocarbon rich stream comprises benzene, toluene, ethyl benzene, and xylene. In certain aspects of the present invention, the hydrogen sulfide concentration in the acid gas stream is between 15% to 55% by volume. In certain aspects of the present invention, the concentration of hydrogen sulfide in the hydrogen sulfide rich stream is greater than 55% by volume.

In a third aspect of the present invention, an enrichment apparatus for enriching a hydrogen sulfide concentration in an acid gas stream to create a hydrogen sulfide rich stream for feed to a Claus unit is provided. The enrichment apparatus includes a hydrocarbon selective separation unit, the hydrocarbon selective separation unit operable to separate the acid gas stream into a hydrocarbon rich stream and a purified acid gas stream, wherein the acid gas stream includes hydrogen sulfide, carbon dioxide, and hydrocarbons. The enrichment apparatus further includes a carbon dioxide selective separation unit in fluid communication with the hydrocarbon selective separation unit, the carbon dioxide selective separation unit operable to separate the purified acid gas stream to create a carbon dioxide rich stream and a carbon dioxide lean stream, the carbon dioxide lean stream having a concentration of hydrogen sulfide, and the Claus unit in fluid communication with the carbon dioxide selective separation unit, the Claus unit operable to recover sulfur from the carbon dioxide lean stream.

In certain aspects of the present invention, the enrichment apparatus further includes a hydrogen sulfide selective separation unit in fluid communication with the carbon dioxide separation unit, the hydrogen sulfide selective separation unit operable to separate the carbon dioxide rich stream to create a hydrogen sulfide rich permeate and a carbon dioxide rich retentate, the hydrogen sulfide rich permeate having a concentration of hydrogen sulfide.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

While the invention will be described with several embodiments, it is understood that one of ordinary skill in the relevant art will appreciate that many examples, variations and alterations to the apparatus and methods described herein are within the scope and spirit of the invention. Accordingly, the exemplary embodiments of the invention described herein are set forth without any loss of generality, and without imposing limitations, on the claimed invention.

Figure 1:
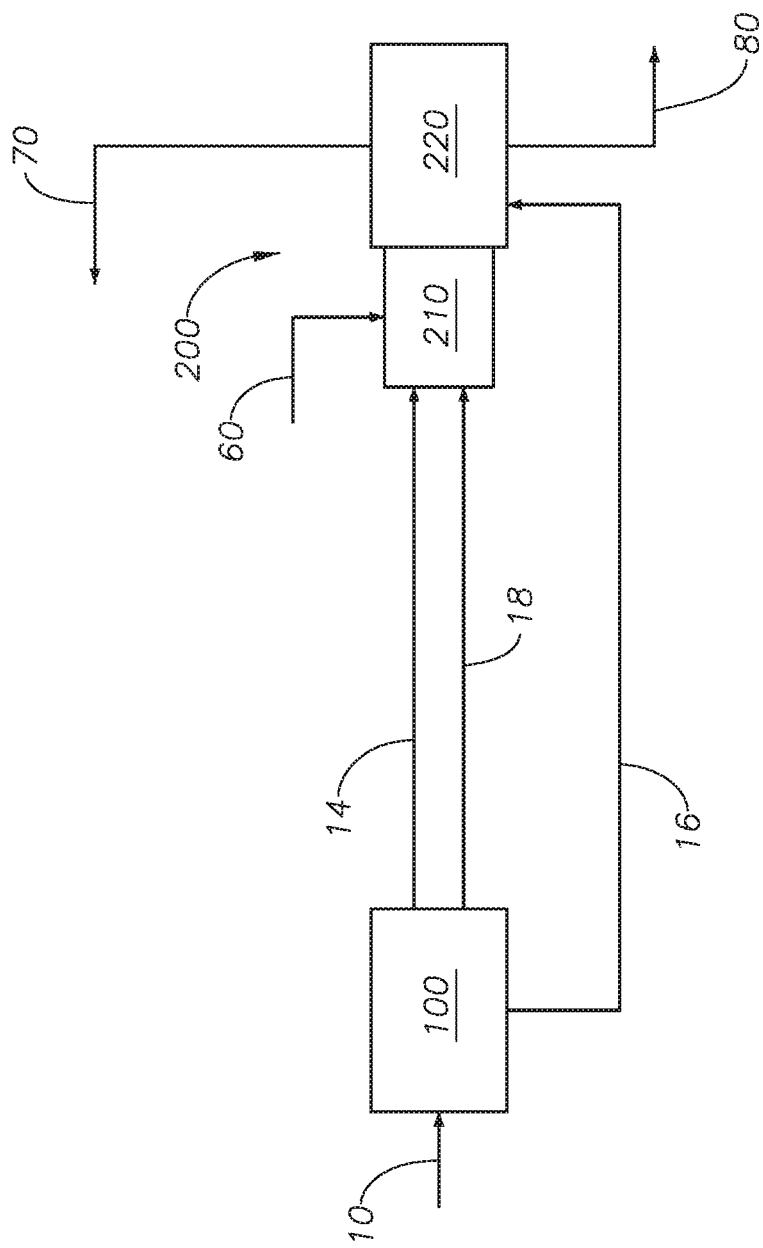
FIG. 1 is a process flow diagram of the present invention.

Referring to FIG. 1, the process flow diagram for enrichment apparatus 100 for enriching the hydrogen sulfide concentration in acid gas stream 10 to create hydrogen sulfide rich stream 18 for feed to Claus unit 200 is provided. Acid gas stream 10 is fed to enrichment apparatus 100. Acid gas stream 10 is any gas stream containing hydrogen sulfide ($H_2S$). In at least one embodiment of the present invention, acid gas stream 10 is from the outlet of an amine unit. In at least one embodiment of the present invention, acid gas stream 10 contains less than about 55% by volume $H_2S$. In some embodiments of the present invention, acid gas stream 10 contains between about 15% and about 55% by volume $H_2S$, alternately between about 15% and about 40% by volume $H_2S$, alternately between about 15% and about 30% by volume $H_2S$, alternately between about 15% and about 25% by volume $H_2S$, alternately between about 15% and about 20% by volume $H_2S$, and alternately between about 25% and about 40% by volume $H_2S$. In at least one embodiment of the present invention, acid gas stream 10 contains greater than 15% by volume $H_2S$. Acid gas stream 10 contains $H_2S$, carbon dioxide ($CO_2$), hydrocarbons, and other contaminants. In at least one embodiment of the present invention, the hydrocarbons present in acid gas stream 10 include benzene, toluene, ethyl benzene, and xylene, collectively referred to as BTEX or BTX. As used herein, BTEX means that a combination of benzene, toluene, ethyl benzene, and xylene are present in a stream, including the absence of one or more of the components. In some embodiments of the present invention, the hydrocarbons present in acid gas stream 10 include alkanes, alkenes, olefins, and BTEX. In some embodiments of the present invention, the contaminants present in acid gas stream 10 include mercaptans, thiols, carbonyl sulfide, carbon disulfide, and combinations thereof.

Enrichment apparatus 100 separates the components of acid gas stream 10 creating a stream rich in $CO_2$, a stream rich in hydrocarbons, and a stream rich in $H_2S$. In at least one embodiment of the present invention, the stream rich in $CO_2$ is hydrogen sulfide lean stream 16, the stream rich in hydrocarbons is hydrocarbon rich stream 14, and the stream rich in $H_2S$ is hydrogen sulfide rich stream 18. Hydrogen sulfide lean stream 16 contains $CO_2$ along with $H_2S$ and other components. Hydrogen sulfide lean stream 16 contains between about 50% and about 99% by volume $CO_2$, alternately between about 75% and about 99% by volume $CO_2$, alternately greater than about 96% by volume $CO_2$. In at least one embodiment of the present invention, hydrogen sulfide lean stream 16 is in the absence of BTEX components. Hydrogen sulfide lean stream 16 is fed to the catalytic converters (not shown) of catalytic stage 220 of Claus unit 200. Feeding hydrogen sulfide lean stream 16 directly to the catalytic converters provides a dilution gas to the catalytic converters and removes a source of carbon for formation of carbonyl sulfide (COS) and carbon disulfide ($CS_2$) in the furnace. The catalytic converter of Claus unit 200 to which hydrogen sulfide lean stream 16 is fed is a function of the concentration of hydrogen sulfide in lean stream 16 or the need for dilution within that catalytic converter.

Hydrocarbon rich stream 14 includes an amount of the BTEX present in acid gas stream 10. Hydrocarbon rich stream 14 includes other hydrocarbons, such as $C_{2+}$ alkanes, alkenes, olefins, and aromatics, $H_2S$, $CO_2$, and other contaminants present in acid gas stream 10. Hydrocarbon rich stream 14 is fed to furnace 210 of Claus unit 200. In some embodiments of the present invention, hydrocarbon rich stream 14 is sent to an alternate disposal operation, such as an incinerator. In some embodiments, hydrocarbon rich stream 14 is sent to a BTX recovery process (not shown) to recover additional hydrocarbons. A BTX recovery process is any process capable of separating BTEX and other hydrocarbons from a process stream. Exemplary processing units for hydrocarbon recovery in a BTX recovery process include condensation, adsorption, and absorption units. The recovered BTEX can be treated further, can be processed for sale, or can be sent to storage.

Hydrogen sulfide rich stream 18 is fed to furnace 210 of Claus unit 200. Hydrogen sulfide rich stream 18 contains an amount of the $H_2S$ present in acid gas stream 10, along with $CO_2$, and hydrocarbons. Hydrogen sulfide rich stream 18 has a greater concentration of $H_2S$ as compared to acid gas stream 10. In some embodiments of the present invention, the $H_2S$ concentration in hydrogen sulfide rich stream 18 is greater than about 25% by volume, alternately greater than about 30% by volume, alternately greater than about 35% by volume, alternately greater than about 40% by volume, alternately greater than about 45% by volume, alternately greater than about 50% by volume, alternately greater than about 55% by volume, alternately greater than about 56% by volume, alternately greater than about 57% by volume, alternately greater than about 58% by volume, and alternately greater than about 60% by volume.

Claus unit 200 uses feed air 60 in furnace 210 to process hydrocarbon rich stream 14 and hydrogen sulfide rich stream 18. In some embodiments of the present invention, hydrocarbon rich stream 14 and hydrogen sulfide rich stream 18 can be separately introduced to furnace 210 of Claus unit 200. In some embodiments of the present invention, hydrocarbon rich stream 14 and hydrogen sulfide rich stream 18 can be combined upstream of furnace 210 of Claus unit 200, such that one combined stream is fed to Claus unit 200. Claus unit 200 produces waste gas stream 70 and elemental sulfur stream 80.

One of skill in the art will appreciate that Claus units are well-known processing systems and the system equipment associated with Claus units can be designed based on the needs and layout of the process site. The present invention can be used with an existing Claus unit or as part of a retrofitted Claus unit, and thus the present invention contemplates that Claus unit 200 contains similar basic elements known to one of skill in the art.

In some embodiments of the present invention, hydrocarbon rich stream 14 and hydrogen sulfide rich stream 18 can be combined (not shown) before being fed to furnace 210.

In embodiments where the streams are combined, the concentration of hydrogen sulfide in the combined stream is greater than about 25% by volume, alternately greater than about 30% by volume, alternately greater than about 35% by volume, alternately greater than about 40% by volume, alternately greater than about 45% by volume, alternately greater than about 50% by volume, alternately greater than about 55% by volume, alternately greater than about 56% by volume, alternately greater than about 57% by volume, alternately greater than about 58% by volume, and alternately greater than about 60% by volume.

In at least one embodiment of the present invention, hydrocarbon rich stream 14 can be fed to a section of furnace 210 having a temperature greater than 950° C., alternately greater than 1000° C., and alternately greater than 1050° C. According to embodiments of the present invention, enrichment apparatus 100 concentrates BTEX and other contaminants in hydrocarbon rich stream 14, concentrates hydrogen sulfide in hydrogen sulfide rich stream 18, and concentrates carbon dioxide in hydrogen sulfide lean stream 16. Concentrating the components in the various streams enables directing the feeds to the appropriate place in the Claus unit for destruction or recovery of components, as the case may be. By way of example, concentrating hydrocarbons and other contaminants in hydrocarbon rich stream 14 allows the stream to be fed directly to a section of furnace 210 with a temperature greater than 950° C. and maintaining a section of furnace 210 at a temperature greater than 950° C. is facilitated because of the concentrated hydrogen sulfide in the hydrogen sulfide rich stream 18.

Figure 2:
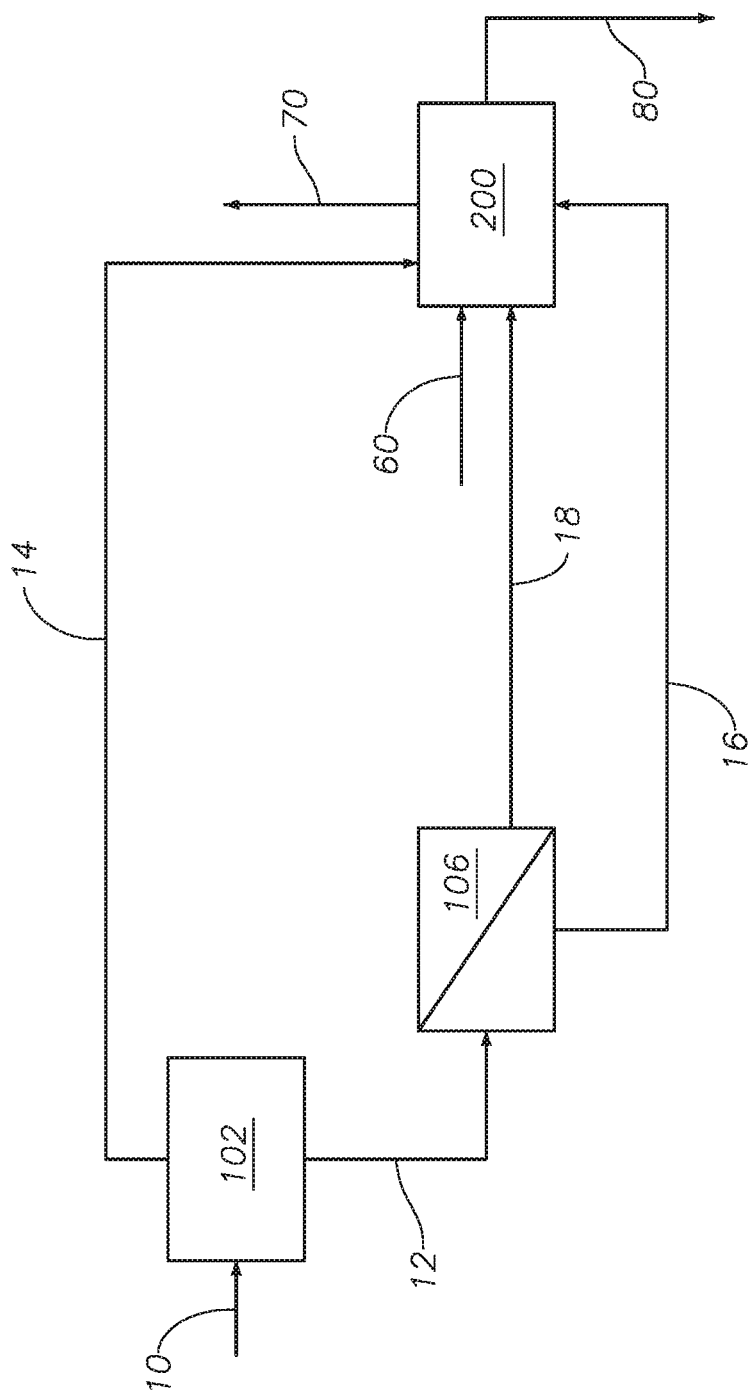
FIG. 2 is a process flow diagram of one embodiment of enrichment apparatus 100.

Referring to FIG. 2, an embodiment of enrichment apparatus 100 is provided. Hydrocarbon selective separation unit 102 separates acid gas stream 10 into hydrocarbon rich stream 14, and purified acid gas stream 12. In at least one embodiment of the present invention, hydrocarbon selective separation unit 102 is a rubbery membrane. As used herein, "rubbery" refers to a polymer having a Young's modulus in the range of $10^5$ to $10^7$ Pa ($10^6$ to $10^8$ dyn/cm$^2$). In at least one embodiment of the present invention, hydrocarbon selective separation unit 102 is a silicone rubber polydimethylsiloxane (PDMS) type rubbery polymer. In at least one embodiment of the present invention, the permeability of the rubbery membrane of carbon dioxide is 3,200 Barrer and the selectivity of toluene to carbon dioxide is 456. In at least one embodiment of the present invention, hydrocarbon selective separation unit 102 is a pressure swing adsorption (PSA) process. In at least one embodiment, the PSA process uses activated carbon as the adsorbent. In at least one embodiment of the present invention, hydrocarbon selective separation unit 102 is a temperature swing adsorption (TSA) process. In at least one embodiment of the present invention, the TSA process uses activated carbon as the adsorbent. In at least one embodiment of the present invention, hydrocarbon selective separation unit 102 is a condensing absorption process. Hydrocarbon rich stream 14 is fed to Claus unit 200 as described with reference to FIG. 1.

Purified acid gas stream 12 contains most of the $H_2S$ and $CO_2$ present in acid gas stream 10. Purified acid gas stream 12 is fed to hydrogen sulfide selective separation unit 106. Hydrogen sulfide selective separation unit 106 separates purified acid gas stream 12 into hydrogen sulfide rich stream 18 as the permeate stream and hydrogen sulfide lean stream 16 as the retentate stream.

Hydrogen sulfide selective separation unit 106 is any membrane capable of separating hydrogen sulfide from acid gas stream 10. Exemplary membranes include membranes based upon polyphosphazenes, polyether-polyamide copolymers, ionic liquid membranes, and ionic liquid membrane contactors.

Ionic liquid membranes are membranes that are doped with liquid ionic compounds. Liquid ionic compounds have a preferential solubility for hydrogen sulfide. Liquid ionic compounds have the structural formula:

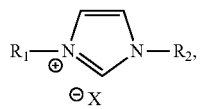

(Formula I)

where $R_1$ is selected from the group consisting of —H, —CH$_2$—CH$_2$—CF$_3$, —CH$_2$—CH$_2$—CH$_2$F, —CH$_3$, —CH$_2$—CH$_3$, propyl, pentyl, hexyl, heptyl, octyl, $C_9$-$C_{18}$ alkyl, alkenyl, and cycloalkyl; $R_2$ is selected from the group consisting of —H, —CH$_2$—CH$_2$—CF$_3$, —CH$_2$—CH$_2$—CH$_2$F, —CH$_3$, —CH$_2$—CH$_3$, propyl, pentyl, hexyl, heptyl, octyl, $C_9$-$C_{18}$ alkyl, alkenyl, and cycloalkyl; and X is selected from the group consisting of BF$_4$, PF$_6$, (CF$_3$SO$_2$)N, CF$_3$(CO)O.

In at least one embodiment of the present invention, the liquid ionic compound of Formula I is where $R_1$ is selected from hydrogen or a $C_1$-$C_{18}$ alkyl group; $R_2$ is selected from a $C_1$-$C_{18}$ alkyl group, a $C_2$-$C_6$ alkenyl, a $C_3$-$C_6$ cycloalkyl, a $C_3$-$C_8$ cycloalkenyl, an aryl, a substituted aryl, aryl ($C_1$-$C_4$ alkyl), or a substituted aryl ($C_1$-$C_4$ alkyl); and X is an anion selected from the group consisting of hydroxide, chloride, bromide, iodide, borate, tetrafluoroborate, cuprate, Cu(I)Cl$_2$ anion, phosphate, hexafluorophosphate, hexafluoroantimonate, perchlorate, nitrite, nitrate, sulfate, a carboxylate, a sulfonate, a sulfonimide, and a phosphonate.

The term "aryl" refers to a cyclic aromatic radical, optionally containing one or more heteroatoms, such as oxygen, nitrogen, and sulfur, such as phenyl, naphthyl, pyridyl, and the like.

The term "substituted aryl" refers to aryl as described herein, where from one to about three hydrogen atoms on the aryl are substituted with monovalent groups, such as halo, alkyl, haloalkyl, alkoxy, haloalkoxy, alkylthio, haloalkylthio, alkylamino, alkanoyl, cyano, nitro, and the like.

Carboxylates useful as anions include alkylcarboxylates, such as acetate, substituted alkylcarboxylates, such as lactate, and haloalkylcarboxylates, such as trifluoroacetate, and the like.

Sulfonates useful as anions include alkylsulfonates, such as mesylate, haloalkylsulfonates, such as triflate and nonaflate, and arylsulfonates, such as tosylate and mesitylate, and the like.

Sulfonimides useful as anions may be mono- or disubstituted sulfonimides, such as methanesulfonimide and bis-ethanesulfonimide, optionally halogenated sulfonimides, such as bis-trifluoromethanesulfonimide, arylsulfonimides, such as bis-(4-methoxybenzene) sulfonamide, and the like.

In a preferred embodiment, hydrogen sulfide selective separation unit 106 includes an ionic liquid membrane impregnated with one or more fluorinated liquid ionic compounds having non-nucleophilic anions.

Exemplary liquid ionic compounds useful for the present invention include imidazolium salts, pyrazolium salts, oxazolium salts, thiazolium salts, triazolium salts, pyridinium salts, pyridazinium salts, pyrimidinium salts, and pyrazinium salts. Illustrative of such compounds are 1-butyl-3-methylimidazolium tetrafluoroborate, 1-ethyl-3-methylimidazolium tetrafluoroborate, 1-butyl-3-methylimidazolium hexafluorophosphate, 1-octyl-3-methylimidazolium hexafluorophosphate, 1-octyl-3-methylimidazolium tetrafluoroborate, 1-butyl-3-methylimidazolium triflate, 1-butyl-3-methylimidazolium trifluoroacetate, and 1-butyl-3-methylimidazolium bis(trifluoromethanesulfonimide), 1-triflluooproyl-3-methylimidazolium bis(trifluoromethanesulfonimide), 1-triflluooproyl-3-methylimidazolium hexafluorophosphate, 1-triflluooproyl-3-methylimidazolium tetrafluoroborate, 1-triflluooproyl-3-methylimidazolium trifluoroacetate and the like. In a preferred embodiment, the fluorinated liquid ionic compound for use in the ionic liquid membrane is 1-butyl-3-methylimidazolium tetrafluoroborate.

One of skill in the art will appreciate that the size, permeability, and selectivity of hydrogen sulfide selective separation unit 106 are design features based on the requirements of the system. The type of membrane selected is in consideration of the desired permeability and selectivity of the membrane and the acid gas feed composition. Membranes suitable for use as hydrogen sulfide selective separation unit 106 are membranes with a H$_2$S/CO$_2$ selectivity from between about 3.0 to about 9.5, alternately between about 3.0 to about 7.0, alternately between about 3.0 to about 5.0.

Hydrogen sulfide rich stream 18 and hydrogen sulfide lean stream 16 are sent to Claus unit 200 as described with reference to FIG. 1.

Figure 3:
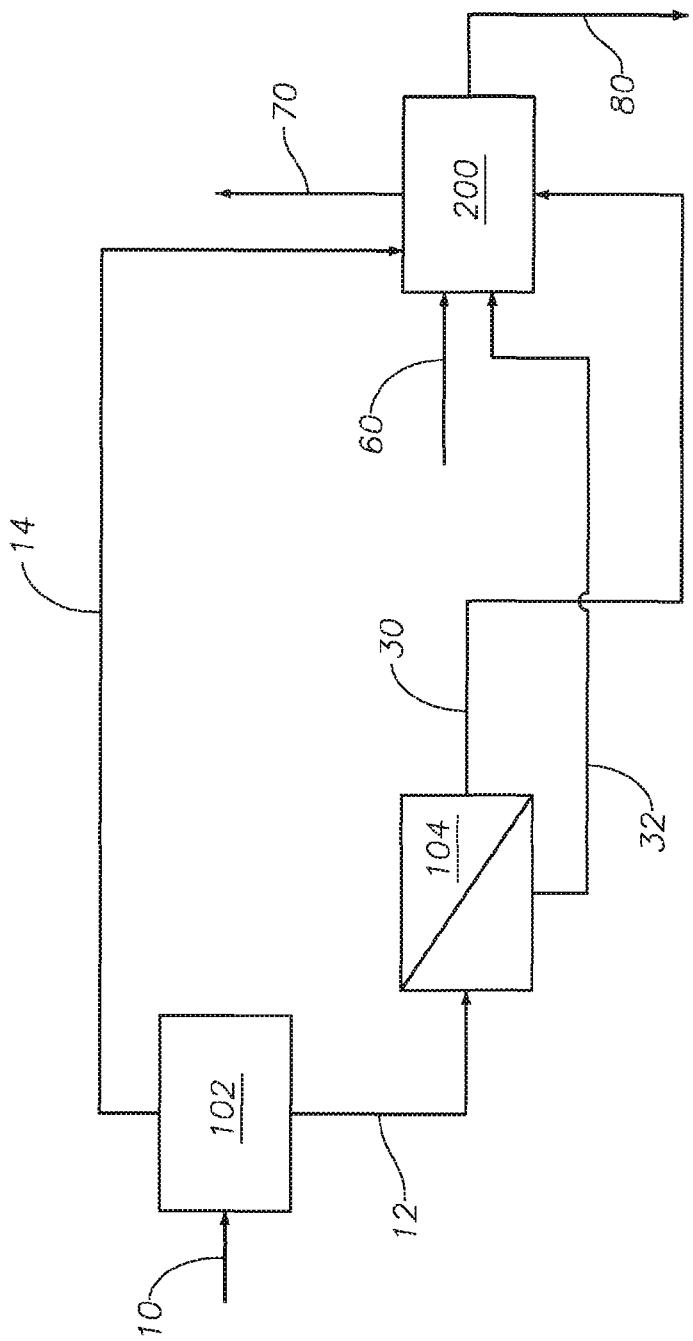
FIG. 3 is a process flow diagram of an embodiment of enrichment apparatus 100.

Referring to FIG. 3, an alternate embodiment of enrichment apparatus 100 is provided. With reference to those elements previously described above, purified acid gas stream 12 is fed to carbon dioxide selective separation unit 104. Carbon dioxide selective separation unit 104 separates purified acid gas stream 12 to create carbon dioxide rich stream 30 in the permeate and carbon dioxide lean stream 32 in the retentate. Carbon dioxide lean stream 32 contains an amount of the H$_2$S present in acid gas stream 10, along with CO$_2$, and hydrocarbons. Carbon dioxide lean stream 32 is fed to the furnace of Claus unit 200. Without being bound to one particular theory, feeding carbon dioxide lean stream 32 and hydrocarbon rich stream 14 to the furnace separately allows mixing of the streams with the flame, which increases combustion and maximizes contaminant destruction. In some embodiments, carbon dioxide lean stream 32 is mixed with hydrocarbon rich stream 14 upstream of the furnace, so that one stream is fed to the furnace. In at least one embodiment of the present invention, the concentration of H$_2$S in carbon dioxide lean stream 32 is greater than 55% by volume.

Carbon dioxide selective separation unit 104 can be any type of separation membrane capable of separating carbon dioxide from acid gas stream 10. Exemplary membranes of carbon dioxide selective separation unit 104 include amorphous fluoroplastic membranes, amorphous perfluoropolymer membranes, and random fluorocopolymer membranes. In at least one embodiment of the present invention, carbon dioxide selective separation unit 104 is a glassy amorphous fluoroplastic membrane, specifically a 2,2 bis(trifluoromethyl)-4,5 difluoro-1,3 dioxole membrane. In at least one embodiment of the present invention, carbon dioxide selective separation unit 104 is a perfluoropolymer membrane, specifically a perfluorocopolymer of tetrafluoroethylene and perfluoromethoxydioxole. In at least one embodiment of the present invention, carbon dioxide selective separation unit 104 is a rubbery random fluorocopolymer membrane of tetrafluoroethylene and perfluoromethyl vinyl ether. Membranes suitable for use as carbon dioxide selective separation unit 104 are membranes with a $CO_2/H_2S$ selectivity from between about 3.0 to about 8.0.

Carbon dioxide rich stream 30 contains $CO_2$, $H_2S$, hydrocarbons, and other contaminants. In at least one embodiment of the present invention, the concentration of $CO_2$ present in carbon dioxide rich stream 30 is greater than 70% by volume, alternately greater than 75% by volume, alternately greater than 80% by volume, alternately greater than 85% by volume, alternately greater than 90%, alternately greater than 95% by volume. Carbon dioxide rich stream 30 is fed to the catalytic converters of Claus unit 200. Feeding carbon dioxide rich stream 30 directly to the catalytic converters provides a dilution gas to the catalytic converters and removes a source of carbon for formation of COS and $CS_2$ in the furnace. The catalytic converter of Claus unit 200 to which carbon dioxide rich stream 30 is fed is a function of the concentration of carbon dioxide in carbon dioxide rich stream 30 or the need for dilution within that catalytic converter.

Figure 4:
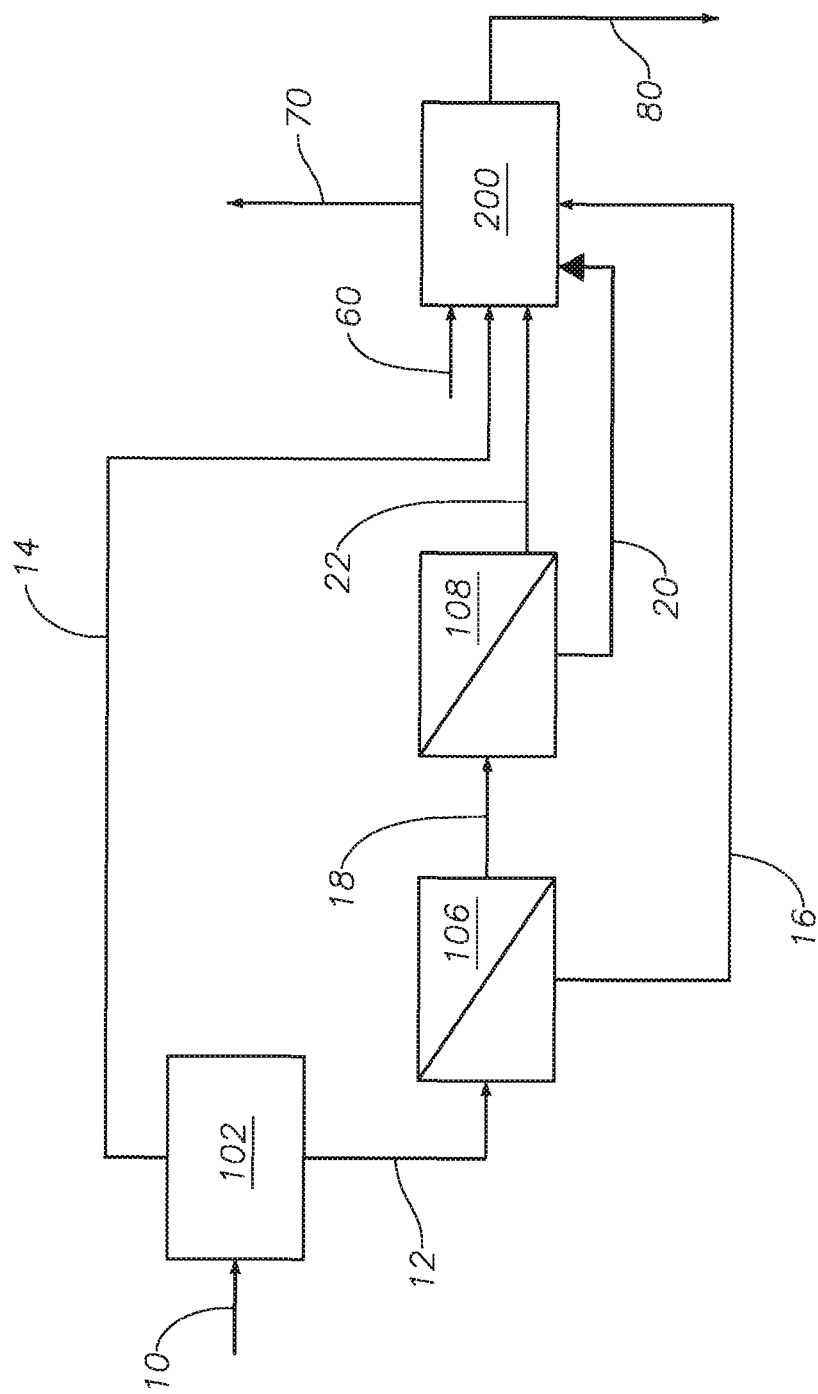
FIG. 4 is a process flow diagram of an embodiment of enrichment apparatus 100.

Referring to FIG. 4, an alternate embodiment of enrichment apparatus 100 is provided. With reference to those elements previously described above, purified acid gas stream 12 is fed to hydrogen sulfide selective separation unit 106. Hydrogen sulfide selective separation unit 106 separates purified acid gas stream 12 into hydrogen sulfide rich stream 18 in the permeate and hydrogen sulfide lean stream 16 in the retentate. Hydrogen sulfide rich stream 18 is fed to second hydrogen sulfide selective separation unit 108. Second hydrogen sulfide selective separation unit 108 separates hydrogen sulfide rich stream 18 into enriched hydrogen sulfide stream 22 in the permeate and carbon dioxide retentate 20 in the retentate. Enriched hydrogen sulfide stream 22 and hydrocarbon rich stream 14 are fed to the furnace of Claus Unit 200. Hydrogen sulfide lean stream 16 and carbon dioxide retentate 20 are fed to the catalytic converters of Claus Unit 200.

Figure 5:
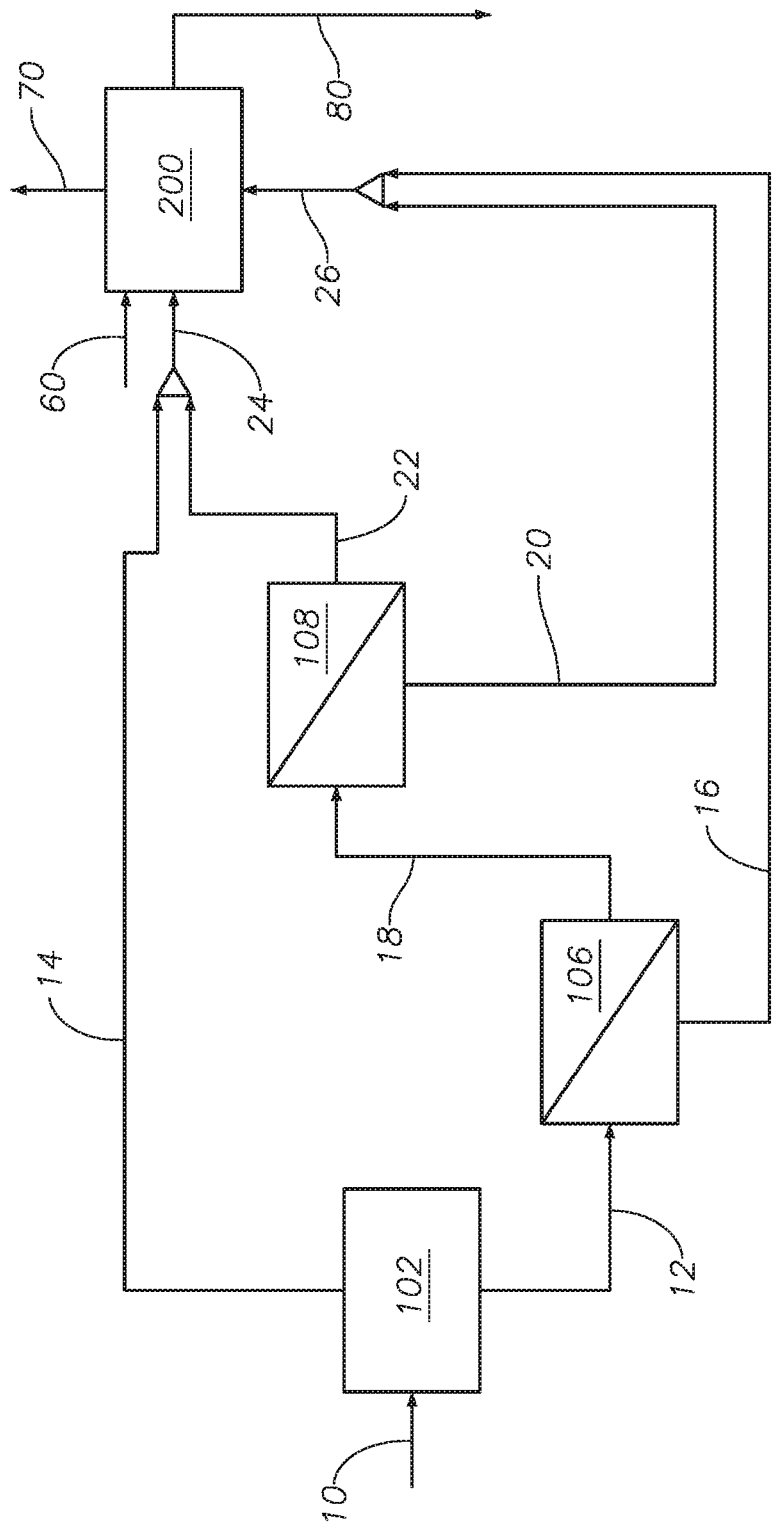
FIG. 5 is a process flow diagram of an embodiment of enrichment apparatus 100.

Referring to FIG. 5, an alternate embodiment of enrichment apparatus 100 is provided. With reference to those elements previously described above, enriched hydrogen sulfide stream 22 and hydrocarbon rich stream 14 are mixed and fed to the furnace of Claus unit 200 as mixed furnace feed stream 24. Hydrogen sulfide lean stream 16 and carbon dioxide retentate 20 are mixed and fed to the catalytic converters of Claus unit 200 as mixed catalytic converter feed stream 26.

Figure 6:
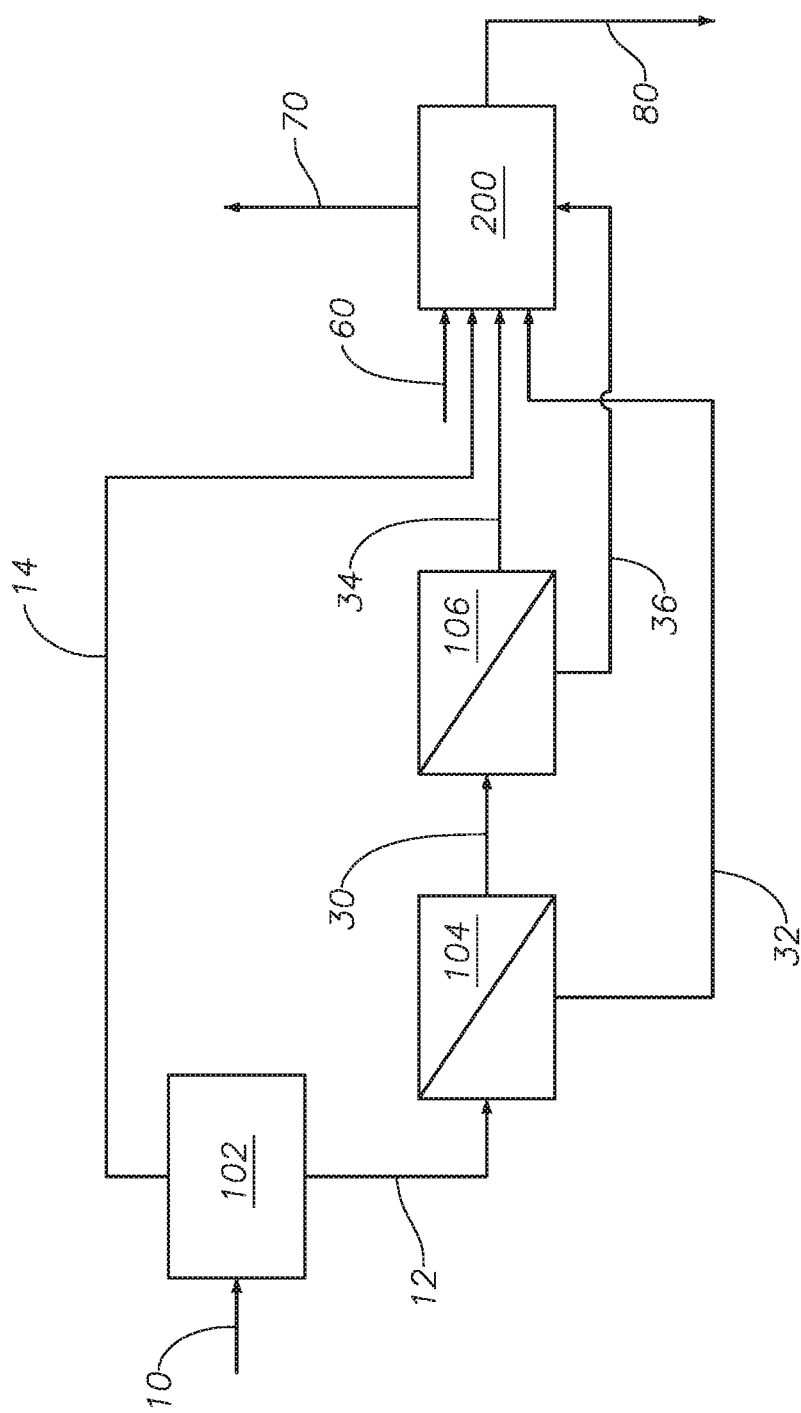
FIG. 6 is a process flow diagram of an embodiment of enrichment apparatus 100.

Referring to FIG. 6, an alternate embodiment of enrichment apparatus 100 is provided. With reference to those elements previously described above, purified acid gas stream 12 is fed to carbon dioxide selective separation unit 104. Carbon dioxide selective separation unit 104 separates purified acid gas stream 12 into carbon dioxide rich stream 30 in the permeate and carbon dioxide lean stream 32 in the retentate. Carbon dioxide rich stream 30 is fed to hydrogen sulfide selective separation unit 106. Hydrogen sulfide selective separation unit 106 separates carbon dioxide rich stream 30 into hydrogen sulfide rich permeate 34 in the permeate and carbon dioxide rich retentate 36 in the retentate. Carbon dioxide lean stream 32, hydrogen sulfide rich permeate 34, and hydrocarbon rich stream 14 are fed to the furnace of Claus Unit 200. Carbon dioxide rich retentate 36 is fed to the catalytic converters of Claus Unit 200.

Figure 7:
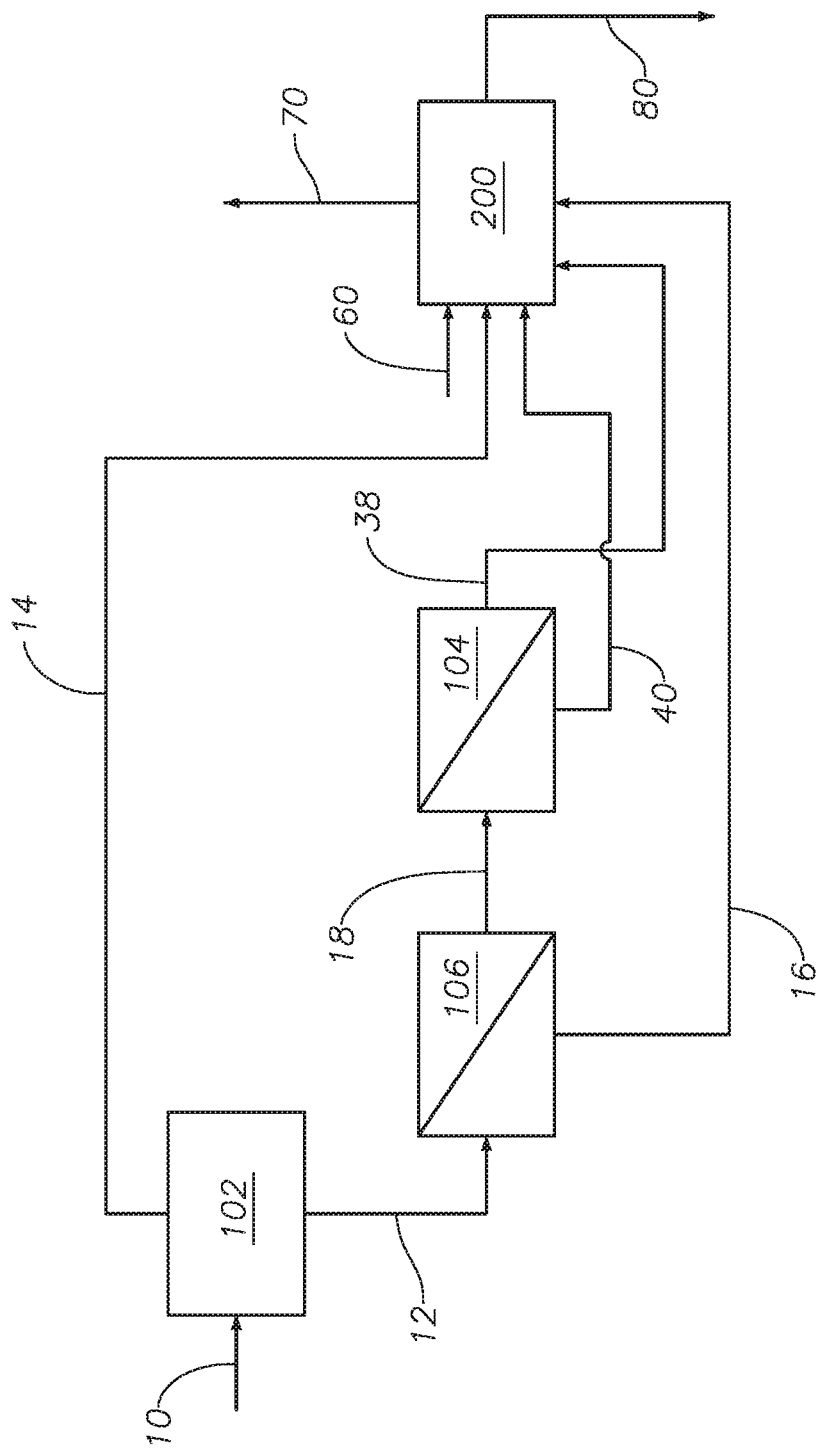
FIG. 7 is a process flow diagram of an embodiment of enrichment apparatus 100.

Referring to FIG. 7, an alternate embodiment of enrichment apparatus 100 is provided. With reference to those elements previously described above, purified acid gas stream 12 is fed to hydrogen sulfide selective separation unit 106. Hydrogen sulfide selective separation unit 106 separates purified acid gas stream 12 into hydrogen sulfide rich stream 18 in the permeate and hydrogen sulfide lean stream 16 in the retentate. Hydrogen sulfide rich stream 18 is fed to carbon dioxide selective separation unit 104. Carbon dioxide selective separation unit 104 separates hydrogen sulfide rich stream 18 into carbon dioxide rich permeate 38 in the permeate and hydrogen sulfide rich retentate 40 in the retentate. Hydrocarbon rich stream 14 and hydrogen sulfide rich retentate 40 are fed to the furnace of Claus Unit 200. Hydrogen sulfide lean stream 16 and carbon dioxide rich permeate 38 are fed to the catalytic converters of Claus Unit 200.

The total number of hydrogen sulfide selective separation units and carbon dioxide selective separation units (hereinafter "separation units") and the configuration of the separation units, including the flow path of the permeate and retentate streams, depends on the composition of acid gas stream 10, and the target concentration of $CO_2$ or $H_2S$ in the feed stream to the furnace or the feed stream to catalytic converters. In at least one embodiment of the present invention, more than two separation units are arranged in series.

The membranes of the present invention are in the absence of methanol. In at least one embodiment of the present invention, hydrogen sulfide selective separation unit 106 is in the absence of a selective solvent absorption process. In at least one embodiment of the present invention, the membranes of the present invention are in the absence of regeneration steps as part of steady state operation.

EXAMPLES

Throughout the examples, references will be made to types of membranes for use in the various separation units. Table 1 includes a list of selected properties for exemplary membranes useful in the separation units of the present invention. The data in Table 1 was collected from independently developed data. Examples of polyether-polyamide copolymers are represented by membranes made with Pebax® polymers. Examples of amorphous fluoroplastics are represented by membranes made using DuPont™ Teflon resins. Polyphosphazene 1, 2, and 3 are copolymers with 2-(2-methoxyethoxy)ethanol (MEE), 4-methoxyphenol and 2-allyphenol.

TABLE 1

Properties of exemplary membranes

| | $CO_2$ permeability (Barrer) | $H_2S$ permeability (Barrer) | $CO_2/H_2S$ Selectivity | $H_2S/CO_2$ Selectivity |
|---|---|---|---|---|
| PDMS | 3,200 | — | 0.63 | 1.6 |
| Pebax ® 1657 | 69 | — | 0.27 | 3.7 |
| Pebax ® 1074 | 122 | — | 0.22 | 4.6 |
| Pebax ® 4011 | 140 | 31 | 0.22 | 4.6 |
| Pebax ® 4011 (pure gas data) | 1750 | 180 | .1028 | 9.5 |
| DuPont ™ 9918 | 28 | — | 8 | 0.125 |
| Teflon ® AF1600 | 580 | — | 6.8 | 0.147 |
| Teflon ® AF2400 | 2,300 | — | 6 | 0.17 |
| Polyphosphazene 1 | 7.5 | 14.1 | 0.53 | 1.89 |
| Polyphosphazene 2 | 152.3 | 587.6 | 0.26 | 3.85 |
| Polyphosphazene 3 | 250 | 1130 | 0.22 | 4.6 |
| BMImBF4 (Ionic Liquid Membrane) | ~6 | ~800 | 0.0075 | 133 |

Table 2 contains the permeation constants for hydrocarbon selective separation unit 102 as used throughout the examples.

TABLE 2

Permeation Constants for Hydrocarbon Selective Separation Unit 102

| Component | Permeation Constant cm$^3$/(cm$^2$ * s * psia) |
|---|---|
| $CO_2$ | 0.31 |
| $H_2S$ | 0.49 |
| BTX | 100.00 |
| $C_5$ | 0.42 |
| $C_4$ | 0.42 |

Example 1

Example 1 was simulated based on the configuration embodied in FIG. 2 and described herein. Acid gas stream 10 from an amine separation process at 37.78° C. and 29.70 psia was fed to hydrocarbon selective separation unit 102 at a rate of 248.52 MMscfd (292.66 Msm$^3$/h). Hydrocarbon selective separation unit 102 was modeled as a PDMS type rubbery polymer membrane with an $H_2S/CO_2$ selectivity of 1.6 and BTX permeability of 100 cm$^3$/(cm$^2$*s*psia). See Table 2 for the permeation constants of the components. Hydrocarbon selective separation unit 102 produced hydrocarbon rich stream 14 in the permeate and purified acid gas stream 12 in the retentate. Purified acid gas stream 12 was then fed to hydrogen sulfide selective separation unit 106. The properties of hydrogen sulfide selective separation unit 106 were modeled after a Pebax® 1657 or polyphosphazene type membrane with an $H_2S/CO_2$ selectivity of 1.6 and BTX permeability of 100 cm$^3$/(cm$^2$*s*psia). Hydrogen sulfide selective separation unit 106 separated purified acid gas stream 12 into hydrogen sulfide rich stream 18 in the permeate and hydrogen sulfide lean stream 16 in the retentate. Hydrogen sulfide rich stream 18 and hydrocarbon rich stream 14 were fed to the furnace of Claus Unit 200. Hydrogen sulfide lean stream 16 was fed to the catalytic converters of Claus Unit 200. The streams to the furnace had a combined $H_2S$ concentration greater than 28%. The resulting concentrations of components % vol for selected streams are shown in Table 3.

TABLE 3

Concentration of Components in Selected Streams, by % vol.

| | Stream 10 | Stream 14 | Stream 18 | Furnace (Streams 14 & 18) | Stream 16 |
|---|---|---|---|---|---|
| Temperature (° C.) | 37.78 | 37.78 | 37.78 | 37.78 | 37.78 |
| Flow Rate (MMscfd) | 248.52 | 9.78 | 186.43 | 196.21 | 52.32 |
| $CO_2$ | 0.747 | 0.644 | 0.717 | 0.714 | 0.872 |
| $H_2S$ | 0.251 | 0.341 | 0.281 | 0.284 | 0.127 |
| BTX | 0.001 | 0.012 | 0.000 | 0.001 | 0.000 |
| $C_5$ | 0.001 | 0.001 | 0.001 | 0.001 | 0.001 |
| $C_4$ | 0.001 | 0.001 | 0.001 | 0.001 | 0.001 |

Example 2

Referring to FIG. 2 and the simulation parameters described in Example 1, in Example 2 hydrogen sulfide selective separation unit 106 was modeled as a rubbery type membrane with a $H_2S/CO_2$ selectivity of 3.18. The permeation constants for hydrogen sulfide selective separation unit 106 for selected components are included in Table 4. Hydrocarbon rich stream 14 and hydrogen sulfide rich stream 18 were fed to the furnace of Claus unit 200. The streams had a combined $H_2S$ concentration of greater than 30%. The resulting concentrations of components by % vol for selected streams are shown in Table 5.

TABLE 4

Permeation Constants - Hydrogen Sulfide Selective Separation Unit 106

| Component | Permeation Constant cm$^3$/(cm$^2$ * s * psia) |
|---|---|
| $CO_2$ | 0.31 |
| $H_2S$ | 0.98 |
| $C_5$ | 0.42 |
| $C_4$ | 0.42 |

TABLE 5

Concentration of Components in Selected Streams, by % vol.

| | Stream 10 | Stream 14 | Stream 18 | Stream 16 | Furnace (Streams 14 and 18) |
|---|---|---|---|---|---|
| Temperature (° C.) | 37.8 | 37.8 | 37.78 | 37.78 | 37.78 |
| Flow Rate (MMscfd) | 248.52 | 9.2 | 186.3 | 53.02 | 195.5 |
| $CO_2$ | 0.747 | 0.485 | 0.694 | 0.977 | 0.684 |
| $H_2S$ | 0.251 | 0.500 | 0.304 | 0.021 | 0.313 |
| BTX | 0.001 | 0.013 | 0.000 | 0.000 | 0.001 |
| $C_5$ | 0.001 | 0.001 | 0.001 | 0.001 | 0.001 |
| $C_4$ | 0.001 | 0.001 | 0.001 | 0.001 | 0.001 |

Example 3

Referring to FIG. 2 and the simulation parameters described in Example 1, in Example 3 hydrogen sulfide selective separation unit 106 was modeled as a Pebax® type membrane with a $H_2S/CO_2$ selectivity of 5.0. The permeation constants for hydrogen sulfide selective separation unit 106 for selected components are provided in Table 6. Hydrocarbon rich stream 14 and hydrogen sulfide rich stream 18 were fed to the furnace of Claus unit 200. The streams had a combined $H_2S$ concentration of greater than about 40%. The resulting concentrations of components for selected streams in vol % are shown in Table 7.

TABLE 6

Permeation Constants - Hydrogen Sulfide Selective Separation Unit 106

| Component | Permeation Constant cm$^3$/(cm$^2$ * s * psia) |
|---|---|
| $CO_2$ | 0.31 |
| $H_2S$ | 1.54 |
| $C_5$ | 0.42 |
| $C_4$ | 0.42 |

TABLE 7

Concentration of Components in Selected Streams, by % vol.

| | Stream 10 | Stream 14 | Stream 18 | Stream 16 | Furnace (Streams 14 & 18) |
|---|---|---|---|---|---|
| Temperature (° C.) | 37.8 | 37.8 | 37.78 | 37.78 | 37.78 |

TABLE 7-continued

Concentration of Components in Selected Streams, by % vol.

|  | Stream 10 | Stream 14 | Stream 18 | Stream 16 | Furnace (Streams 14 & 18) |
|---|---|---|---|---|---|
| Flow Rate (MMscfd) | 248.52 | 9.05 | 135.3 | 104.16 | 144.34 |
| $CO_2$ | 0.747 | 0.380 | 0.601 | 0.968 | 0.587 |
| $H_2S$ | 0.251 | 0.606 | 0.397 | 0.030 | 0.410 |
| BTX | 0.001 | 0.013 | 0.000 | 0.000 | 0.001 |
| $C_5$ | 0.001 | 0.001 | 0.001 | 0.001 | 0.001 |
| $C_4$ | 0.001 | 0.001 | 0.001 | 0.001 | 0.001 |

Example 4

Example 4 was simulated as hydrocarbon selective separation unit 102 coupled with a one-step carbon dioxide selective separation unit 104 as shown in FIG. 3. Acid gas stream 10 at 37.78° C. and 29.70 psia was fed to hydrocarbon selective separation unit 102. Hydrocarbon selective separation unit 102 was modeled as a PDMS type rubbery polymer membrane with a $H_2S/CO_2$ selectivity of 1.6 and BTX permeability of 100 cm³/(cm²*s*psia). See Table 2 for permeation constants for hydrocarbon selective separation unit 102. Hydrocarbon selective separation unit 102 separated acid gas stream 10 into hydrocarbon rich stream 14 in the permeate and purified acid gas stream 12 in the retentate. Purified acid gas stream 12 was fed to carbon dioxide selective separation unit 104. Carbon dioxide selective separation unit 104 was modeled as a glassy type membrane with a $CO_2/H_2S$ selectivity of 6. Permeation constants for carbon dioxide selective separation unit 104 for select components are provided in Table 8. Carbon dioxide selective separation unit 104 separated purified acid gas stream 12 into carbon dioxide rich stream 30 in the permeate and carbon dioxide lean stream 32 in the retentate. Carbon dioxide lean stream 32 and hydrocarbon rich stream 14 were fed to the furnace of Claus Unit 200. Carbon dioxide rich stream 30 was fed to the catalytic converters of Claus Unit 200. The streams to the furnace had a combined $H_2S$ concentration greater than 30%. The resulting concentrations of components for selected streams are shown in Table 9.

TABLE 8

Permeation Constants - Carbon Dioxide Selective Separation Unit 104

| Component | Permeation Constant cm³/(cm² * s * psia) |
|---|---|
| $CO_2$ | 1.2 |
| $H_2S$ | 0.2 |
| $C_5$ | 0.2 |
| $C_4$ | 0.2 |

TABLE 9

Concentration of Components in Selected Streams, by % vol.

|  | Stream 10 | Stream 14 | Stream 30 | Stream 32 | Furnace (Streams 14 & 32) |
|---|---|---|---|---|---|
| Temperature (° C.) | 37.8 | 37.8 | 37.78 | 37.78 | 35.76 |
| Flow Rate (MMscfd) | 248.5 | 9.8 | 54.14 | 184.6 | 194.38 |
| $CO_2$ | 0.7469 | 0.6441 | 0.9402 | 0.6956 | 0.6931 |
| $H_2S$ | 0.2506 | 0.3411 | 0.0594 | 0.3019 | 0.3069 |
| BTX | 0.0010 | 0.0125 | 0.0000 | 0.0000 | 0.0006 |
| $C_5$ | 0.0010 | 0.0012 | 0.0002 | 0.0012 | 0.0012 |
| $C_4$ | 0.0010 | 0.0012 | 0.0002 | 0.0012 | 0.0012 |

Example 5

Referring to FIG. 4, a process diagram of the layout used to model Example 5 is provided. Acid gas stream 10 from an amine separation process at 37.78° C. and 29.70 psia was fed to hydrocarbon selective separation unit 102 at a rate of 248.47 MMscfd (274.23 Msm³/h). Hydrocarbon selective separation unit 102 was modeled as a PDMS type rubbery polymer membrane, with an $H_2S/CO_2$ selectivity of 1.6 and a BTX permeability of 100 cm³/(cm²*s*psia). See Table 2 for the permeation constants of selected components. Hydrocarbon selective separation unit 102 separated acid gas stream 10 into hydrocarbon rich stream 14 in the permeate and purified acid gas stream 12 in the retentate. Purified acid gas stream 12 was then sent to hydrogen sulfide selective separation unit 106. The properties of hydrogen sulfide selective separation unit 106 were modeled after a Pebax® 1657 or polyphosphazene type membrane with an $H_2S/CO_2$ selectivity of 3.99. Permeation constants for selected components in hydrogen sulfide selective separation unit 106 are contained in Table 10. Hydrogen sulfide selective separation unit 106 separated purified acid gas stream 12 into hydrogen sulfide rich stream 18 in the permeate and hydrogen sulfide lean stream 16 in the retentate. Hydrogen sulfide rich stream 18 was fed to second hydrogen sulfide selective separation unit 108. The properties of second hydrogen sulfide selective separation unit 108 were modeled after a Pebax® 1657 or polyphosphazene type membrane with an $H_2S/CO_2$ selectivity of 3.99. Permeation constants for selected components in second hydrogen sulfide selective separation unit 108 are contained in Table 10. Second hydrogen sulfide selective separation unit 108 separated hydrogen sulfide rich stream 18 into enriched hydrogen sulfide stream 22 in the permeate and carbon dioxide retentate 20 in the retentate.

TABLE 10

Permeation Constants - Hydrogen Sulfide Selective Separation Unit 106 and Second Hydrogen Sulfide Selective Separation Unit 108

| Component | Permeation Constant cm³/(cm² * s * psia) |
|---|---|
| $CO_2$ | 0.31 |
| $H_2S$ | 1.23 |
| $C_5$ | 0.42 |
| $C_4$ | 0.42 |

Enriched hydrogen sulfide stream 22 and hydrocarbon rich stream 14 were fed to the furnace of Claus Unit 200. Hydrogen sulfide lean stream 16 and carbon dioxide retentate 20 were fed to the catalytic converters of Claus Unit 200. The streams to the furnace had a combined $H_2S$ concentration greater than 55%. Table 11 shows the composition of select streams in % vol.

TABLE 11

Concentration of Components in Selected Streams, by % vol.

| | Stream 10 | Stream 14 | Stream 16 | Stream 18 | Furnace (Streams 14 & 22) |
|---|---|---|---|---|---|
| Temperature (° C.) | 37.78 | 37.78 | 37.78 | 37.78 | 39.99 |
| Flow Rate (MMscfd) | 248.47 | 9.13 | 63.13 | 176.19 | 152.42 |
| $CO_2$ | 0.6404 | 0.3129 | 0.9659 | 0.5409 | 0.4354 |
| $H_2S$ | 0.3571 | 0.6731 | 0.0320 | 0.4571 | 0.5620 |
| BTX | 0.0005 | 0.0127 | 0.0000 | 0.0000 | 0.0008 |
| $C_5$ | 0.0010 | 0.0007 | 0.0011 | 0.0010 | 0.0009 |
| $C_4$ | 0.0010 | 0.0007 | 0.0011 | 0.0010 | 0.0009 |

Example 6

Referring to FIG. 5 and the simulation parameters described with reference to Example 5, in Example 6 hydrogen sulfide selective separation unit 106 and second hydrogen sulfide selective separation unit 108 were modeled after a Pebax® 4011, Pebax® 1074, polyphosphazene type membrane, or an ionic liquid membrane/ionic liquid membrane contactors type membrane with an $H_2S/CO_2$ selectivity of 5.0. Table 12 contains the permeation constants for hydrogen sulfide selective separation unit 106 and second hydrogen sulfide selective separation unit 108.

TABLE 12

Permeation Constants - Hydrogen Sulfide Selective Separation Unit 106 and Second Hydrogen Sulfide Selective Separation Unit 108

| Component | Permeation Constant $cm^3/(cm^2 * s * psia)$ |
|---|---|
| $CO_2$ | 0.31 |
| $H_2S$ | 1.54 |
| $C_5$ | 0.42 |
| $C_4$ | 0.42 |

Enriched hydrogen sulfide stream 22 and hydrocarbon rich stream 14 are mixed and fed to the furnace of Claus unit 200 as mixed furnace feed stream 24. Mixed furnace feed stream 24 has an $H_2S$ concentration of greater than 55%. Hydrogen sulfide lean stream 16 and carbon dioxide retentate 20 are mixed and fed to the catalytic converters of Claus unit 200 as mixed catalytic converter feed stream 26. The resulting concentrations of components for selected streams by % volume are shown in Table 13.

TABLE 13

Concentration of Components in Selected Streams, by % vol.

| | Stream 10 | Stream 16 | Stream 14 | Stream 18 | Stream 24 | Stream 26 |
|---|---|---|---|---|---|---|
| Temperature (° C.) | 37.78 | 37.78 | 37.78 | 37.78 | 37.78 | 37.78 |
| Flow Rate (MMscfd) | 248.52 | 52.32 | 9.78 | 186.43 | 145.3 | 103.14 |
| $CO_2$ | 0.6404 | 0.9663 | 0.2721 | 0.5985 | 0.4109 | 0.9641 |
| $H_2S$ | 0.3571 | 0.0019 | 0.7176 | 0.3994 | 0.5865 | 0.0336 |
| BTX | 0.0005 | 0.0000 | 0.0092 | 0.0000 | 0.0008 | 0.0000 |
| $C_5$ | 0.0010 | 0.0009 | 0.0006 | 0.0010 | 0.0009 | 0.0012 |
| $C_4$ | 0.0010 | 0.0009 | 0.0006 | 0.0010 | 0.0009 | 0.0012 |

Example 7

Example 7 was simulated based on the configuration embodied in FIG. 6. Acid gas stream 10 at 37.78° C. and 29.70 psia was fed to hydrocarbon selective separation unit 102 at a rate of 248.5 MMscfd (292.66 $Msm^3/h$). Hydrocarbon selective separation unit 102 was modeled as a PDMS type rubbery polymer membrane with an $H_2S/CO_2$ selectivity of 1.6 and a BTX permeability of 100 $cm^3/(cm^2*s*psia)$. Hydrocarbon selective separation unit 102 separated acid gas stream 10 into hydrocarbon rich stream 14 in the permeate and purified acid gas stream 12 in the retentate. Purified acid gas stream 12 was then fed to carbon dioxide selective separation unit 104. Carbon dioxide selective separation unit 104 was modeled as a glassy type membrane with a $CO_2/H_2S$ selectivity of 6. Carbon dioxide selective separation unit 104 separated purified acid gas stream 12 into carbon dioxide rich stream 30 in the permeate and carbon dioxide lean stream 32 in the retentate. Carbon dioxide rich stream 30 is fed to hydrogen sulfide selective separation unit 106. Hydrogen sulfide selective separation unit 106 is a Pebax® 4011, Pebax® 1074, polyphosphazene based, ionic liquid membrane, or ionic liquid membrane contactor type membrane with an $H_2S/CO_2$ selectivity of 5.0. Permeation constants for carbon dioxide selective separation unit 104 and hydrogen sulfide selective separation unit 106 are contained in Table 14 for select components. Hydrogen sulfide selective separation unit 106 separated carbon dioxide rich stream 30 into hydrogen sulfide rich permeate 34 in the permeate and carbon dioxide rich retentate 36 in the retentate. Carbon dioxide lean stream 32, hydrogen sulfide rich permeate 34, and hydrocarbon rich stream 14 were fed to the furnace of Claus Unit 200. Carbon dioxide rich retentate 36 was fed to the catalytic converters of Claus Unit 200. The streams to the furnace had a combined $H_2S$ concentration greater than 40%. The resulting concentrations of components for selected streams by % volume are shown in Table 15.

TABLE 14

Permeation Constants

| Component | Carbon dioxide selective separation unit 104 $cm^3/(cm^2 * s * psia)$ | Hydrogen Sulfide Selective Separation Unit 106 $cm^3/(cm^2 * s * psia)$ |
|---|---|---|
| $CO_2$ | 1.2 | 0.31 |
| $H_2S$ | 0.2 | 1.54 |
| $C_5$ | 0.2 | 0.3 |
| $C_4$ | 0.2 | 0.3 |

TABLE 15

Concentration of Components in Selected Streams, by % vol.

| | Stream 10 | Stream 14 | Stream 30 | Stream 34 | Furnace (Streams 14, 32, & 34) | Stream 36 |
|---|---|---|---|---|---|---|
| Temperature (° C.) | 37.8 | 37.8 | 37.78 | 37.78 | 37.78 | 37.78 |
| Flow Rate (MMscfd) | 248.47 | 10.78 | 50.04 | 15.77 | 214.2 | 34.27 |
| $CO_2$ | 0.6404 | 0.5248 | 0.9041 | 0.5768 | 0.5879 | 0.9688 |
| $H_2S$ | 0.3571 | 0.4611 | 0.0954 | 0.4208 | 0.4093 | 0.0306 |
| BTX | 0.0005 | 0.0112 | 0.0000 | 0.0000 | 0.0006 | 0.0000 |
| $C_5$ | 0.0010 | 0.0011 | 0.0003 | 0.0012 | 0.0011 | 0.0003 |
| $C_4$ | 0.0010 | 0.0011 | 0.0003 | 0.0012 | 0.0011 | 0.0003 |

Example 8

Example 8 was simulated based on the configuration embodied in FIG. 7. Acid gas stream 10 at 37.78° C. and 29.70 psia was fed to hydrocarbon selective separation unit 102 at a rate of 248.5 MMscfd (292.66 Msm³/h). Hydrocarbon selective separation unit 102 was modeled as a PDMS type rubbery polymer membrane with an $H_2S/CO_2$ selectivity of 1.6 and a BTX permeability of 100 cm³/(cm²*s*psia). Hydrocarbon selective separation unit 102 separated acid gas stream 10 into hydrocarbon rich stream 14 in the permeate and purified acid gas stream 12 in the retentate. Purified acid gas stream 12 was then fed to hydrogen sulfide selective separation unit 106. The properties of hydrogen sulfide selective separation unit 106 were modeled after a Pebax® 4011, Pebax® 1074, polyphosphazene type, ionic liquid membrane, or an ionic liquid membrane contactor type membrane with a $H_2S/CO_2$ selectivity of 5.0. Hydrogen sulfide selective separation unit 106 separated purified acid gas stream 12 into hydrogen sulfide rich stream 18 in the permeate and hydrogen sulfide lean stream 16 in the retentate. Hydrogen sulfide rich stream 18 was fed to carbon dioxide selective separation unit 104. Carbon dioxide selective separation unit 104 was modeled as a glassy type membrane with a $CO_2/H_2S$ selectivity of 6.0. Permeation constants for hydrogen sulfide selective separation unit 106 and carbon dioxide selective separation unit 104 are contained in Table 16. Carbon dioxide selective separation unit 104 separated hydrogen sulfide rich stream 18 into carbon dioxide rich permeate 38 in the permeate and hydrogen sulfide rich retentate 40 in the retentate. Hydrocarbon rich stream 14 and hydrogen sulfide rich retentate 40 were fed to the furnace of Claus Unit 200. Hydrogen sulfide lean stream 16 and carbon dioxide rich permeate 38 were fed to the catalytic converters of Claus Unit 200. The streams to the furnace had a combined $H_2S$ concentration greater than 68%. The resulting concentrations of components for selected streams by % volume are shown in Table 17.

TABLE 16

Permeation Constants

| Component | Carbon dioxide selective separation unit 104 cm³/(cm² * s * psia) | Hydrogen Sulfide Selective Separation Unit 106 cm³/(cm² * s * psia) |
|---|---|---|
| $CO_2$ | 1.2 | 0.31 |
| $H_2S$ | 0.2 | 1.54 |
| $C_5$ | 0.2 | 0.3 |
| $C_4$ | 0.2 | 0.3 |

TABLE 17

Concentration of Components in Selected Streams, by % vol.

| | Stream 10 | Stream 16 | Stream 14 | Furnace (Streams 14 & 40) | Cat. Converters (Streams 16 & 38) |
|---|---|---|---|---|---|
| Temperature (° C.) | 37.78 | 37.78 | 37.78 | 37.78 | 37.78 |
| Flow Rate (MMscfd) | 248.5 | 134.2 | 10.8 | 92.4 | 156.1 |
| $CO_2$ | 0.6404 | 0.8518 | 0.5248 | 0.3090 | 0.8366 |
| $H_2S$ | 0.3571 | 0.1456 | 0.4617 | 0.6880 | 0.1609 |
| BTX | 0.0005 | 0.0000 | 0.0112 | 0.0013 | 0.0000 |
| $C_5$ | 0.0010 | 0.0013 | 0.0011 | 0.0007 | 0.0012 |
| $C_4$ | 0.0010 | 0.0013 | 0.0011 | 0.0007 | 0.0012 |

Example 9

Example 9 observed the effect of membrane surface on the concentration of components in selected streams. Referring to FIG. 7 and the simulation parameters described with reference to Example 8, in Example 9 the membranes used for hydrogen sulfide selective separation unit 106 and carbon dioxide selective separation unit 104 were modeled with a total surface area 1.55 times the surface area used in Example 8. The streams to furnace had a combined $H_2S$ concentration greater than 58%. The streams to the catalytic converters had a combined $H_2S$ of less than 7.2%.

TABLE 18

Concentration of Components in Selected Streams, by % vol.

| | Stream 10 | Stream 16 | Stream 14 | Furnace (Streams 14 & 40) | Cat. Converters (Streams 16 & 38) |
|---|---|---|---|---|---|
| Temperature (° C.) | 37.78 | 37.78 | 37.78 | 37.72 | 36.8 |
| Flow Rate (MMscfd) | 248.5 | 82.5 | 10.8 | 139.2 | 109.2 |
| $CO_2$ | 0.6404 | 0.9581 | 0.5248 | 0.4168 | 0.9259 |
| $H_2S$ | 0.3571 | 0.0389 | 0.4617 | 0.5806 | 0.0718 |
| BTX | 0.0005 | 0.0000 | 0.0112 | 0.0009 | 0.0000 |
| $C_5$ | 0.0010 | 0.0015 | 0.0011 | 0.0008 | 0.0012 |
| $C_4$ | 0.0010 | 0.0015 | 0.0011 | 0.0008 | 0.0012 |

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

What is claimed:

1. An enrichment apparatus for enriching a hydrogen sulfide concentration in an acid gas stream to create a hydrogen sulfide rich stream for feed to a Claus unit, the enrichment apparatus comprising:
    a hydrocarbon selective separation unit, the hydrocarbon selective separation unit operable to separate the acid gas stream into a hydrocarbon rich stream and a purified acid gas stream,
        wherein the acid gas stream comprises aromatics selected from the group consisting of benzene, toluene, ethyl benzene, xylenes and combinations thereof; and
    a hydrogen sulfide selective separation unit in fluid communication with the hydrocarbon selective separation unit, the hydrogen sulfide selective separation unit operable to separate the purified acid gas stream to create the hydrogen sulfide rich stream and a hydrogen sulfide lean stream, the hydrogen sulfide rich stream having a concentration of hydrogen sulfide.

2. The enrichment apparatus of claim 1, further comprising:
    a carbon dioxide selective separation unit in fluid communication with the hydrogen sulfide selective separation unit, the carbon dioxide selective separation unit operable to separate the hydrogen sulfide rich stream to create a carbon dioxide rich permeate and a hydrogen sulfide rich retentate, the hydrogen sulfide rich retentate having a concentration of hydrogen sulfide.

3. The enrichment apparatus of claim 2, wherein the carbon dioxide selective separation unit is selected from the group consisting of an amorphous fluoroplastic membrane, an amorphous perfluoropolymer membrane, a random fluorocopolymer membrane, a perfluorinated copolymer membrane, and combinations thereof.

4. The enrichment apparatus of claim 1, further comprising
    a second hydrogen sulfide selective separation unit in fluid communication with the hydrogen sulfide selective separation unit, the second hydrogen sulfide selective separation unit operable to separate the hydrogen sulfide rich stream to create an enriched hydrogen sulfide stream and a carbon dioxide retentate.

5. The enrichment apparatus of claim 1, wherein the hydrogen sulfide selective separation unit is selected from the group consisting of polyphosphazene type polymer membranes, polyether-polyamide copolymer membranes, ionic liquid membranes, ionic liquid membrane contactors, and combinations thereof.

6. The enrichment apparatus of claim 5, wherein the second hydrogen sulfide selective separation unit is selected from the group consisting of polyphosphazene type polymer membranes, polyether-polyamide copolymer membranes, ionic liquid membranes, ionic liquid membrane contactors, and combinations thereof.

7. The enrichment apparatus of claim 1, wherein the hydrocarbon selective separation unit comprises a PDMS type rubbery polymer membrane.

8. The enrichment apparatus of claim 1, wherein the acid gas stream further comprises contaminants selected from the group consisting of mercaptans, thiols, carbonyl sulfide, carbon disulfide, and combinations thereof.

9. The enrichment apparatus of claim 1, wherein the hydrogen sulfide concentration in the acid gas stream is between 15% to 55% by volume.

10. The enrichment apparatus of claim 1, wherein the concentration of hydrogen sulfide in the hydrogen sulfide rich stream is greater than 55% by volume.

11. The enrichment apparatus of claim 1, further including a mixer operable to mix the hydrocarbon rich stream and the hydrogen sulfide rich stream into a feed stream for a furnace of the Claus unit.

12. The enrichment apparatus of claim 11, wherein the concentration of hydrogen sulfide in the feed stream for the furnace of the Claus unit is greater than 25% by volume.

13. A process for enriching a hydrogen sulfide concentration in an acid gas stream to create a hydrogen sulfide rich stream for feeding to a Claus unit, the process comprising the steps of:
    feeding the acid gas stream to a hydrocarbon selective separation unit, the acid gas stream comprising hydrogen sulfide, carbon dioxide, and hydrocarbons;
    separating the acid gas stream in the hydrocarbon selective separation unit to create a hydrocarbon rich stream and a purified acid gas stream, wherein the hydrocarbon rich stream comprises aromatics selected from the group consisting of benzene, toluene, ethyl benzene, xylene, and combinations thereof;
    feeding the purified acid gas stream to a hydrogen sulfide selective separation unit fluidly connected to the hydrocarbon selective separation unit, the hydrogen sulfide selective separation unit operable to separate the purified acid gas stream; and
    separating the purified acid gas stream in the hydrogen sulfide selective separation unit to create the hydrogen sulfide rich stream and a hydrogen sulfide lean stream, the hydrogen sulfide rich stream having a concentration of hydrogen sulfide.

14. The process of claim 13, further comprising the steps of:
    feeding the hydrogen sulfide rich stream to a carbon dioxide selective separation unit in fluid communication with the hydrogen sulfide selective separation unit, the carbon dioxide selective separation unit operable to separate the hydrogen sulfide rich stream;
    separating the hydrogen sulfide rich stream to create a carbon dioxide rich permeate and a hydrogen sulfide rich retentate, the hydrogen sulfide rich retentate having a concentration of hydrogen sulfide; and feeding the hydrogen sulfide rich retentate to the furnace of the Claus unit.

15. The process of claim 14, wherein the carbon dioxide selective separation unit is selected from the group consisting of an amorphous fluoroplastic membrane, an amorphous perfluoropolymer membrane, a random fluorocopolymer membrane, a perfluorinated copolymer membrane, and combinations thereof.

16. The process of claim 13, further comprising the steps of:

feeding the hydrogen sulfide rich stream to a second hydrogen sulfide selective separation unit fluidly connected to hydrogen sulfide selective separation unit, the second hydrogen sulfide selective separation unit operable to separate the hydrogen sulfide rich stream; and separating the hydrogen sulfide rich stream in the second hydrogen sulfide selective separation unit to create an enriched hydrogen sulfide stream and a carbon dioxide retentate.

17. The process of claim 16, further comprising the steps of:

mixing the hydrocarbon rich stream and the enriched hydrogen sulfide stream to create a mixed furnace feed stream; and feeding the mixed furnace feed stream to a furnace of the Claus unit.

18. The process of claim 17, wherein the mixed furnace feed stream has a hydrogen sulfide concentration of at least 25% by volume.

19. The process of claim 13, wherein the hydrogen sulfide selective separation unit is selected from the group consisting of polyphosphazene type polymer membranes, polyether-polyamide copolymer membranes, ionic liquid membranes, ionic liquid membrane contactors, and combinations thereof.

20. The process of claim 13, wherein the hydrocarbon selective separation unit comprises a PDMS type rubbery polymer membrane.

21. The process of claim 13, wherein the acid gas stream further comprises contaminants is selected from the group consisting of mercaptans, thiols, carbonyl sulfide, carbon disulfide, and combinations thereof.

22. The process of claim 13, wherein the hydrogen sulfide concentration in the acid gas stream is between 15% to 55% by volume.

23. The process of claim 13, wherein the hydrogen sulfide rich stream has a hydrogen sulfide concentration greater than 55% by volume.

24. An enrichment apparatus for enriching a hydrogen sulfide concentration in an acid gas stream to create a hydrogen sulfide rich stream for feed to a Claus unit, the enrichment apparatus comprising:

a hydrocarbon selective separation unit, the hydrocarbon selective separation unit operable to separate the acid gas stream into a hydrocarbon rich stream and a purified acid gas stream,
 wherein the acid gas stream comprises hydrogen sulfide, carbon dioxide, and hydrocarbons,
 wherein the hydrocarbon rich stream comprises aromatics selected from the group consisting of benzene, toluene, ethyl benzene, xylene, and combinations thereof; and a carbon dioxide selective separation unit in fluid communication with the hydrocarbon selective separation unit, the carbon dioxide selective separation unit operable to separate the purified acid gas stream to create a carbon dioxide rich stream and a carbon dioxide lean stream, the carbon dioxide lean stream having a concentration of hydrogen sulfide.

25. The enrichment apparatus of claim 24, further comprising:

a hydrogen sulfide selective separation unit in fluid communication with the carbon dioxide selective separation unit, the hydrogen sulfide selective separation unit operable to separate the carbon dioxide rich stream into a hydrogen sulfide rich permeate and a carbon dioxide rich retentate, the hydrogen sulfide rich permeate having a concentration of hydrogen sulfide.

26. A process for enriching a hydrogen sulfide concentration in an acid gas stream to create a hydrogen sulfide rich stream for feed to a Claus unit, the process comprising the steps of:

feeding the acid gas stream to a hydrocarbon selective separation unit, the acid gas stream comprising hydrogen sulfide, carbon dioxide, and hydrocarbons;

separating the acid gas stream in the hydrocarbon selective separation unit to create a hydrocarbon rich stream and a purified acid gas stream, wherein the hydrocarbon rich stream comprises aromatics selected from the group consisting of benzene, toluene, ethyl benzene, xylene, and combinations thereof;

feeding the purified acid gas stream to a carbon dioxide selective separation unit fluidly connected to the hydrocarbon selective separation unit, the carbon dioxide selective separation unit operable to separate the purified acid gas stream; and separating the purified acid gas stream in the carbon dioxide selective separation unit to create a carbon dioxide rich stream and a carbon dioxide lean stream, the carbon dioxide lean stream having a concentration of hydrogen sulfide.

27. The process of claim 26, further including the step of:

feeding the carbon dioxide rich stream to a hydrogen sulfide selective separation unit fluidly connected to the carbon dioxide selective separation unit, the hydrogen sulfide selective separation unit operable to separate the carbon dioxide rich stream; and separating the carbon dioxide rich in the hydrogen sulfide selective separation unit to produce a hydrogen sulfide rich permeate and a carbon dioxide rich retentate, the hydrogen sulfide rich permeate having a concentration of hydrogen sulfide.

28. The process of claim 26, wherein the acid gas stream further comprises contaminants is selected from the group consisting of mercaptans, thiols, carbonyl sulfide, carbon disulfide, and combinations thereof.

29. The process of claim 26, wherein the hydrogen sulfide concentration in the acid gas stream is between 15% to 55% by volume.

30. The process of claim 26, wherein the hydrogen sulfide rich stream has a hydrogen sulfide concentration greater than 55% by volume.

* * * * *